United States Patent
Brument

(10) Patent No.: US 12,351,832 B2
(45) Date of Patent: *Jul. 8, 2025

(54) RECOMBINANT ADENO-ASSOCIATED VIRUS PARTICLE PURIFICATION WITH MULTIPLE-STEP ANION EXCHANGE CHROMATOGRAPHY

(71) Applicants: INSTITUT NATIONAL DE LA SANTE ET DE LA RECHERCHE MEDICALE (INSERM), Paris (FR); NANTES UNIVERSITE, Nantes (FR); CHU NANTES, Nantes (FR); ASSOCIATION FRANCAISE CONTRE LES MYOPATHIES, Paris (FR)

(72) Inventor: Nicole Brument, Nantes (FR)

(73) Assignees: INSTITUT NATIONAL DE LA SANTE ET DE LA RECHERCHE MEDICALE (INSERM), Paris (FR); UNIVERSITE DE NANTES, Nantes (FR); CHU NANTES, Nantes (FR); ASSOCIATION FRANCAISE CONTRE LES MYOPATHIES, Paris (FR)

( * ) Notice: Subject to any disclaimer, the term of this patent is extended or adjusted under 35 U.S.C. 154(b) by 599 days.

This patent is subject to a terminal disclaimer.

(21) Appl. No.: 17/526,467

(22) Filed: Nov. 15, 2021

(65) Prior Publication Data

US 2022/0098618 A1 Mar. 31, 2022
US 2024/0060054 A9 Feb. 22, 2024

Related U.S. Application Data

(63) Continuation of application No. 15/549,279, filed as application No. PCT/EP2016/052739 on Feb. 9, 2016, now Pat. No. 11,203,740.

(30) Foreign Application Priority Data

Feb. 9, 2015 (EP) .................................... 15305187

(51) Int. Cl.
| | |
|---|---|
| *C12N 7/02* | (2006.01) |
| *B01D 15/36* | (2006.01) |
| *B01D 69/02* | (2006.01) |
| *C12N 7/00* | (2006.01) |
| *C12N 15/86* | (2006.01) |
| *A61K 48/00* | (2006.01) |

(52) U.S. Cl.
CPC ............ *C12N 7/02* (2013.01); *B01D 15/363* (2013.01); *B01D 69/02* (2013.01); *C12N 7/00* (2013.01); *C12N 15/86* (2013.01); *A61K 48/00* (2013.01); *B01D 2257/91* (2013.01); *B01D 2325/34* (2013.01); *C12N 2750/14121* (2013.01); *C12N 2750/14143* (2013.01); *C12N 2750/14151* (2013.01)

(58) Field of Classification Search
CPC . C12N 7/02; C12N 7/00; C12N 15/86; C12N 2750/14121; C12N 2750/14143; C12N 2750/14151; B01D 15/363; B01D 2325/34; A61K 48/00
See application file for complete search history.

(56) References Cited

U.S. PATENT DOCUMENTS

| | | | |
|---|---|---|---|
| 5,139,941 A | 8/1992 | Muzyczka et al. | |
| 5,173,414 A | 12/1992 | Lebkowski et al. | |

(Continued)

FOREIGN PATENT DOCUMENTS

| | | |
|---|---|---|
| WO | 1992001070 A1 | 1/1992 |
| WO | 1993003769 A1 | 3/1993 |

(Continued)

OTHER PUBLICATIONS

Allocca et al. "AAV-mediated gene replacement, either alone or in combination with physical and pharmacological agents, results in partial and transient protection from photoreceptor degeneration associated with BPDE deficiency." Investigative ophthalmology & visual science 52.8 (2011): 5713-5719. (Year: 2011).*

Qu, Weihong, et al. "Scalable downstream strategies for purification of recombinant adeno-associated virus vectors in light of the properties." Current pharmaceutical biotechnology 16.8 (2015): 684-695. (Year: 2015).*

Allocca et al. "AAV-mediated gene replacement, either alone or in combination with physical and pharmacological agents, results in partial and transient protection from photoreceptor degeneration associated with βPDE deficiency." Investigative ophthalmology & visual science 52.8 (2011): 5713-5719. (Year: 2011).*

(Continued)

*Primary Examiner* — Maria G Leavitt
*Assistant Examiner* — Michael Angelo Riga
(74) *Attorney, Agent, or Firm* — WCF IP

(57) ABSTRACT

A method for obtaining purified recombinant Adeno-Associated Virus particles (rAAV) is provided. The method includes steps of: a) performing a depth filtration of a cell lysate or a culture supernatant obtained from cells producing rAAV particles, whereby a rAAV-containing clarified composition is provided; b) submitting the rAAV-containing clarified composition to a first step of anion-exchange chromatography on a chromatographic support wherein the rAAV-containing fraction is collected, whereby a first rAAV enriched composition is provided; c) submitting the first rAAV enriched composition at least once to a second step of anion-exchange chromatography on a chromatographic support wherein the rAAV-containing fraction is collected, whereby a second rAAV enriched composition is provided; d) submitting the second rAAV enriched composition to a step of tangential flow filtration to provide purified recombinant Adeno-Associated Virus particles (rAAV).

8 Claims, 5 Drawing Sheets

Specification includes a Sequence Listing.

(56) References Cited

U.S. PATENT DOCUMENTS

| | | | |
|---|---|---|---|
| 6,376,237 | B1 | 4/2002 | Colosi |
| 7,419,817 | B2 | 9/2008 | Chiorini et al. |
| 7,625,570 | B1 | 12/2009 | Schaffer et al. |
| 2001/0043916 | A1 | 11/2001 | McNeilly et al. |
| 2004/0106184 | A1* | 6/2004 | Senesac .................. C12N 7/00 435/239 |

FOREIGN PATENT DOCUMENTS

| | | | |
|---|---|---|---|
| WO | 2002012455 | A1 | 2/2002 |
| WO | 2003097797 | A2 | 12/2003 |
| WO | 2004020971 | | 3/2004 |
| WO | 2004113494 | A2 | 12/2004 |
| WO | 2007059473 | | 5/2007 |
| WO | 2007134325 | | 11/2007 |
| WO | 2010130753 | A1 | 11/2010 |
| WO | 2010148143 | A1 | 12/2010 |
| WO | 2011066454 | A1 | 6/2011 |
| WO | 2011094198 | | 8/2011 |
| WO | 2012010280 | A1 | 1/2012 |

OTHER PUBLICATIONS

Oksanen, Hanna M., Ausra Domanska, and Dennis H. Bamford. "Monolithic ion exchange chromatographic methods for virus purification." Virology 434.2 (2012): 271-277. (Year: 2012).*

Le Meur, G., Stieger, K., Smith, A. et al. Restoration of vision in RPE65-deficient Briard dogs using an AAV serotype 4 vector that specifically targets the retinal pigmented epithelium. Gene Ther 14, 292-303 (2007). (Year: 2007).*

Gao et al. "Empty virions in AAV8 vector preparations reduce transduction efficiency and may cause total viral particle dose-limiting side effects." Molecular Therapy—Methods & Clinical development, 2014, 1(9):20139.

Uchida et al. "Early Life Stress Enhances Behavioral Vulnerability to Stress through the Activation of REST4-Mediated Gene Transcription in the Medial Prefrontal Cortex of Rodents." The Journal of Neuroscience, Nov. 10, 2010, 30(45):15007-15018.

Allay et al. "Good manufacturing practice production of self-complementary serotype 8 adeno-associated viral vector for a hemophilia B clinical trial." Human gene therapy (2011) vol. 22,5: 595-604.

Allocca et al., "AAV-mediated gene replacement, either alone or in combination with physical and pharmacological agents, results in partial and transient protection from photoreceptor degeneration associated with betaPDE deficiency". Invest Ophthalmol Vis Sci. Jul. 29, 2011;52(8):5713-9.

Ayuso et al., "Manufacturing and characterization of a recombinant adeno-associated virus type 8 reference standard material". Hum Gene Ther. Nov. 2014;25(11):977-87.

Berns & Bohensky, 1987. "Adeno-associated viruses: an update". In Maramorosch, Murphy, & Shatkin (Eds.), Advances in Virus Research (vol. 32, pp. 243-307). New York, NY: Academic Press, Inc.

Blouin et al. "Improving rAAV production and purification: towards the definition of a scaleable process." The journal of gene medicine vol. 6 Suppl 1 (2004): S223-8.

Brument et al., "A versatile and scalable two-step ion-exchange chromatography process for the purification of recombinant adeno-associated virus serotypes-2 and -5". Mol Ther. Nov. 2002;6(5):678-86.

Carter, "Adeno-associated virus vectors". Curr Opin Biotechnol. Oct. 1992;3(5):533-9.

Chu et al., "SV40 DNA transfection of cells in suspension: analysis of efficiency of transcription and translation of T-antigen". Gene. Mar. 1981;13(2):197-202.

Heukeshoven & Dernick, "Characterization of a solvent system for separation of water-insoluble poliovirus proteins by reversed-phase high-performance liquid chromatography". J Chromatogr. Jun. 19, 1985; 326:91-101.

Kotin, "Prospects for the use of adeno-associated virus as a vector for human gene therapy". Hum Gene Ther. Jul. 1994;5(7):793-801.

Le Meur et al., "Restoration of vision in RPE65-deficient Briard dogs using an AAV serotype 4 vector that specifically targets the retinal pigmented epithelium". Gene Ther. Feb. 2007;14(4):292-303.

Lebkowski et al., "Adeno-associated virus: a vector system for efficient introduction and integration of DNA into a variety of mammalian cell types". Mol Cell Biol. Oct. 1988;8(10):3988-96.

McCarty et al., "Sequences required for coordinate induction of adeno-associated virus p19 and p40 promoters by Rep protein". J Virol. Jun. 1991;65(6):2936-45.

Muzyczka, "Use of adeno-associated virus as a general transduction vector for mammalian cells". Curr Top Microbiol Immunol. 1992; 158:97-129.

Oksanen et al., "Monolithic ion exchange chromatographic methods for virus purification". Virology. Dec. 20, 2012;434(2):271-7.

Petit et al., "Restoration of vision in the pde6β-deficient dog, a large animal model of rod-cone dystrophy". Mol Ther. Nov. 2012;20(11):2019-30.

Qu et al. "Separation of adeno-associated virus type 2 empty particles from genome containing vectors by anion-exchange column chromatography." Journal of virological methods (2007) vol. 140,1-2: 183-92.

Salvetti et al., "Factors influencing recombinant adeno-associated virus production". Hum Gene Ther. Mar. 20, 1998;9(5):695-706.

Samulski et al., "Helper-free stocks of recombinant adeno-associated viruses: normal integration does not require viral gene expression". J Virol. Sep. 1989;63(9):3822-8.

Toublanc et al. "Identification of a replication-defective herpes simplex virus for recombinant adeno-associated virus type 2 (rAAV2) particle assembly using stable producer cell lines." The journal of gene medicine vol. 6,5 (2004): 555-64.

Urabe et al. "Removal of empty capsids from type 1 adeno-associated virus vector stocks by anion-exchange chromatography potentiates transgene expression." Molecular therapy: the journal of the American Society of Gene Therapy (2006) vol. 13,4: 823-8.

Wang et al. "Production and purification of recombinant adeno-associated vectors." Methods in molecular biology (Clifton, N.J.) vol. 807 (2011): 361-404.

Zhou et al. "PEG-modulated column chromatography for purification of recombinant adeno-associated virus serotype 9." Journal of virological methods, Apr. 2011, vol. 173,1: 99-107.

Burova, E. & Ioffe, E., "Chromatographic purification of recombinant adenoviral and adeno-associated viral vectors: methods and implications", Gene Therapy 12, 2005.

Merck Millipore, "Data Sheet: Polysep II Filters".

Potter, M. et al., "A simplified purification protocol for recombinant adeno-associated virus vectors", Molecular Therapy—Methods & Clinical Development 1, 2014.

Clément, N, & Grieger, J., "Manufacturing of recombinant adeno-associated viral vectors for clinical trials", Molecular Therapy—Methods & Clinical Development 3, 2016.

Qu, G. et al., "Separation of adeno-associated virus type 2 empty particles from genome containing vectors by anion-exchange column chromatography", Journal of Virological Methods 140, 2007.

GE Healthcare, "Ion Exchange Chromatography & Chromatofocusing Principles and Methods", 2010.

Nestola, P. et al., "Improved Virus Purification Processes for Vaccines and Gene Therapy", Biotechnology and Bioengineering 112:5, 2015.

Pall Corporation, "Profile UP Filters", Filtration. Separation. Solution., 2011.

Lajmi, A. et al., "A Membrane Chromatography Application: A Rapid, High Capacity Gene Therapy Vector Purification Tool", Taylor & Francis Group, 2007.

Li, X. et al., "Gene Therapy Rescues Cone Structure and Function in the 3-Month-Old rd12 Mouse: A Model for Midcourse RPE65 Leber Congenital Amaurosis", Investigative Ophthalmology & Visual Science, Jan. 2011, vol. 52, No. 1.

* cited by examiner

RECOMBINANT ADENO-ASSOCIATED VIRUS PARTICLE PURIFICATION WITH MULTIPLE-STEP ANION EXCHANGE CHROMATOGRAPHY

CROSS-REFERENCE TO RELATED APPLICATIONS

This application is a continuation application of U.S. Ser. No. 15/549,279, now U.S. Pat. No. 11,203,740, which was a Rule 371 filing from PCT/EP2016/052739 filed Feb. 9, 2016, which claimed priority to European Application 15305187.5 filed Feb. 9, 2015.

FIELD OF THE INVENTION

The invention relates to the field of purification of Adeno-Associated Virus particles (rAAVs). In particular, it relates to methods for obtaining purified recombinant Adeno-Associated Virus particles (rAAV). It also relates to purified rAAV particles and compositions thereof which are obtainable using said methods. It further relates to AAV plasmids, and host cells which have been transfected with said plasmids, and also rAAV particles produced by said host cells.

BACKGROUND OF THE INVENTION

Gene delivery is a promising method for the treatment of acquired and inherited diseases. A number of viral-based systems for gene transfer purposes have been described, including Adeno-Associated Virus (AAV)-based systems. AAV is a helper-dependent DNA parvovirus that belongs to the genus Dependovirus. AAV requires co-infection with an unrelated helper virus, e.g., adenovirus, herpes virus, or vaccinia, in order for a productive infection to occur. In the absence of a helpervirus, AAV establishes a latent state by inserting its genome into a host cell chromosome. Subsequent infection by a helper virus rescues the integrated viral genome, which can then replicate to produce infectious viral progeny.

AAV has a wide host range and is able to replicate in cells from any species in the presence of a suitable helper virus. For example, human AAV will replicate in canine cells co-infected with a canine adenovirus. AAV has not been associated with any human or animal disease and does not appear to alter the biological properties of the host cell upon integration. For a review of AAV, see, e.g., Berns and Bohenzky (1987) Advances in Virus Research (Academic Press, Inc.) 32:243-307.

Le meur et al. ("*Restoration of vision in RPE65-deficient Briard dogs using an AAV serotype 4 vector that specifically targets the retinal pigmented epithelium*"; Gene Therapy; Vol. 14, 292-303; 2007) teaches the use of an rAAV for restoring vision in a RPE65-deficient Dog.

Petit et al. ("*Restoration of vision in the pde6β-deficient Dog, a Large Animal Model of Rod-cone Dystrophy*"; Molecular Therapy "; Vol. 20, no. 11, 2019-2030"; 2012) teaches the use of an rAAV, for restoring vision in a PDE6β-deficient Dog.

For all those reasons, the use of Adeno-Associated Virus for gene therapy has been proposed. However, applications are still lacking due to the requirement for preparations having sufficient purity and/or infectivity for clinical use.

Thus, there remains a need for novel methods for purifying Adeno-Associated Virus particles (rAAVs). In particular, there remains a need for scalable methods which are well-defined, reproducible, and within controlled environmental conditions in accordance with Good Manufacturing Practices (GMP).

In particular, there remains a need for methods for purifying Adeno-Associated Virus particles (rAAVs) which require a limited number of steps.

There also remains a need for methods for purifying Adeno-Associated Virus particles (rAAVs) which are suitable for use as a medicament, and/or gene therapy.

Thus, there remains a need for scalable methods for purifying rAAV particles and compositions thereof, with high purity and infectivity.

Methods for purifying Adeno-Associated Virus particles have been reported in the prior Art. However, those methods are not necessarily satisfying for producing rAAV particles which are directly suitable for use as a medicament and/or for gene therapy.

WO2011/094198 teaches a method for purifying AAV particles, including a step of Ion Exchange Column Chromatography and a step of Tangential Flow Filtration.

WO03/097797 teaches a method for purifying virus particles with reduced contaminating DNA levels, which may include steps of cell lysis, depth filtration and/or centrifugation, ultracentrifugation, nuclease treatment, anion exchange chromatography and tangential flow filtration.

On the other hand, many of the available techniques have the disadvantage to require prior extensive treatment of the cell extracts, including density gradient, treatment with nucleases and detergents before the chromatography step. Such additional treatments render the whole process less satisfactory at an industrial scale.

Brument et al. ("*A Versatile and Scalable Two-Step Ion-Exchange Chromatography Process for the Purification of Recombinant Adeno-associated Virus Serotypes-2 and -5*"; Molecular Therapy; Vol. 6, No. 5; 2002) teaches a two-step chromatography process for the purification of rAAV2 or rAAV5, including a step of cation exchange chromatography followed by a step of anion-exchange chromatography.

However there remains a need for novel methods which can be scaled up with respect to good manufacturing practice issues, which remain acceptable from an economic point of view, and suitable for use as a medicament or for gene therapy.

There also remains a need for novel purified rAAV particles and compositions thereof, as such and/or for use as a medicament or for gene therapy, which can be further purified by said processes, and which remain suitable for producing rAAV particles in a given host cell.

SUMMARY OF THE INVENTION

The present invention relates to method for obtaining purified recombinant Adeno-Associated Virus particles (rAAV), comprising the steps of:
  a) performing a depth filtration of a starting material previously obtained from cells producing rAAV particles, the said starting material being selected in a group comprising a cell lysate and a culture supernatant, whereby a rAAV-containing clarified composition is provided;
  b) submitting the rAAV-containing clarified composition to a first step of anion-exchange chromatography on a chromatographic support wherein elution is performed by using a linear salt gradient and wherein the rAAV-containing fraction is collected, whereby a first rAAV enriched composition is provided;

c) submitting the first rAAV enriched composition at least once to a second step of anion-exchange chromatography on a chromatographic support wherein elution is performed by using a linear salt gradient and wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

The invention also relates to purified rAAV particles that are obtained by performing the method described above. It further relates to a purified rAAV particle composition comprising at least one purified rAAV particle as defined above.

It further relates to said purified rAAV particles and to compositions thereof, for use for gene therapy and/or for the preparation of a medicament for use for gene therapy.

The invention also relates to an AAV plasmid comprising an expression cassette encoding human PDE6-beta, and to a host cell transfected with said AAV plasmid, and further to rAAV particles which are produced by said host cell.

DETAILED DESCRIPTION OF THE INVENTION

Figure 1A:
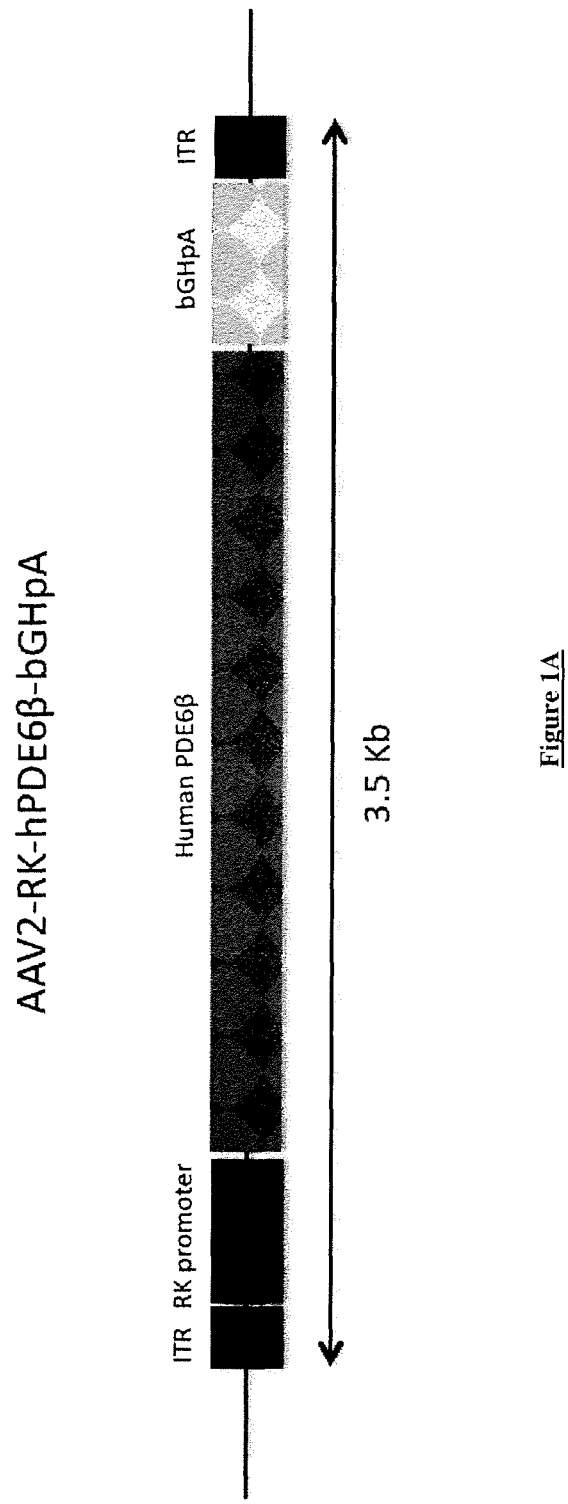
FIG. 1A: Cartography of the expression cassette of an AAV plasmid encoding human PDE6β. The nucleic acid sequence coding for the human PDE6β protein is associated at its 5' end to a human rhodopsine kinase (RK) promoter and at its 3' end to a bovine growth hormone polyadenylation site (bGHpA), flanked by Inverted Terminal Repeat (ITR) sequences.

The invention addresses the aforementioned needs.

The current invention provides a recombinant Adeno-Associated Virus (rAAV) particle purification method that includes two unique features that distinguish it from current "industry-standard" scalable AAV particles purification processes: 1) a modular platform process that can be used for purification of different AAV serotypes/capsid variants with high purity, and which is suitable for producing preparations directly suitable for clinical applications; and 2) a unique sequence of process steps, including at least two anion-exchange chromatography steps, which are performed by using a linear salt gradient.

Surprisingly those characteristics confer unexpected scalability, for purifying a starting material such as a cell lysate or a culture supernatant. In particular, this process has the advantage of being suitable for pH optimization, in order to prepare purified recombinant Adeno-Associated Virus particles having optimal infectiosity, and which are suitable for gene therapy.

Without wishing to be bound by any particular theory, the inventors are of the opinion that selectivity of a given anion-exchange chromatography support for rAAV preparations depends on the quality of the product that is passed through: thus, a cleaner product, will result in a better separation of compounds on the support. Thus, the use of two or more, preferably consecutive, anion-chromatography steps will lead to optimal separation of compounds on said support, and is thus suitable for isolating rAAV particles in an improved manner.

Advantageously, the composition is eluted on the anion-exchange chromatography support using a linear salt gradient. Without wishing to be bound by any particular theory, the inventors are also of the opinion that the linear salt gradient provides more efficient separation of the eluted species, compared to step salt gradients. The difference lies in the lower slope of the gradient, which allows for the formation of a slow increase in salt concentration, and thus optimal separation of rAAV particles within the chromatography support.

To the best of the knowledge of the inventors, it is the first described "industry-standard" method for purifying clinical-grade rAAV particles, in particular rAAV particles belonging to the AAV4 and/or AAV5 serotype, which involves a two-step anion-exchange chromatography using a linear salt gradient.

Also, residual DNA at the end of the process is in accordance with clinical standards, even in the absence of treatment with detergents and nucleases, including DNAses.

Thus, the invention relates to a method for obtaining purified recombinant Adeno-Associated Virus particles (rAAV), and is particularly suitable for purifying rAAV particles belonging to a AAV serotype selected in a group comprising, or consisting of, AAV1, AAV2, AAV3, AAV4, AAV5, AAV8, AAV9, AAV10, and rhesus macaque-derived serotypes including AAVrh10, and mixtures thereof; in particular AAV4 and AAV5, and most preferably AAV5.

According to a first embodiment, the invention relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition to a first step of anion-exchange chromatography on a chromatographic support wherein elution is performed by using a linear salt gradient and wherein the rAAV-containing fraction is collected, whereby a first rAAV enriched composition is provided;

c) submitting the first rAAV enriched composition at least once to a second step of anion-exchange chromatography on a chromatographic support wherein elution is performed by using a linear salt gradient and wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

The starting material may comprise either rAAV particles belonging to one serotype, or belonging to a plurality of serotypes, including rAAV particles belonging to the AAV4 and/or AAV5 serotype.

According to an alternative embodiment, the invention relates to a method for obtaining purified recombinant Adeno-Associated Virus particles (rAAV) of the AAV4 serotype, comprising the steps of:

a) performing a depth filtration of a starting material previously obtained from cells producing rAAV particles, the said starting material being selected in a group comprising a cell lysate and a culture supernatant, whereby a rAAV4-containing clarified composition is provided;

b) submitting the rAAV4-containing clarified composition to a first step of anion-exchange chromatography on a chromatographic support wherein elution is performed by using a linear salt gradient and wherein the rAAV4-containing fraction is collected, whereby a first rAAV4 enriched composition is provided;

c) submitting the first rAAV4 enriched composition at least once to a second step of anion-exchange chromatography on a chromatographic support wherein elution is performed by using a linear salt gradient and wherein the rAAV4-containing fraction is collected, whereby a second rAAV4 enriched composition is provided;

d) submitting the second rAAV4 enriched composition to a step of tangential flow filtration, whereby purified recombinant Adeno-Associated Virus particles (rAAV) of the AAV4 serotype are provided.

According to another alternative embodiment, the invention relates to a method for obtaining purified recombinant Adeno-Associated Virus particles (rAAV) of the AAV5 serotype, comprising the steps of:

a) performing a depth filtration of a starting material previously obtained from cells producing rAAV particles, the said starting material being selected in a group comprising a cell lysate and a culture supernatant, whereby a rAAV5-containing clarified composition is provided;

b) submitting the rAAV5-containing clarified composition to a first step of anion-exchange chromatography on a chromatographic support wherein elution is performed by using a linear salt gradient and wherein the rAAV5-containing fraction is collected, whereby a first rAAV5 enriched composition is provided;

c) submitting the first rAAV5-enriched composition at least once to a second step of anion-exchange chromatography on a chromatographic support wherein elution is performed by using a linear salt gradient and wherein the rAAV5-containing fraction is collected, whereby a second rAAV5 enriched composition is provided;

d) submitting the second rAAV5 enriched composition to a step of tangential flow filtration, whereby purified recombinant Adeno-Associated Virus particles (rAAV) of the AAV5 serotype are provided.

The purified rAAV particles of the invention comprise a heterologous nucleic acid encoding a desirable gene product. Such products include without limitation, siRNAs, antisense molecules, miRNAs, ribozymes and the like. Other products include nucleic acids encoding hormones, growth receptors, ligands and proteins useful for gene therapy.

According to a second embodiment, the invention relates to a purified rAAV particle obtained by performing the method as described above, and to compositions thereof.

According to a third embodiment, the invention relates to said purified rAAV particles and to compositions thereof, for use for gene therapy.

According to a fourth embodiment, the invention relates to an AAV plasmid comprising an expression cassette encoding human PDE6-beta, to a host cell which has been transfected with said AAV plasmid, and to rAAV particles produced by the host cell, as such and also for use for gene therapy.

According to the invention, the expression "comprising", such as in "comprising the steps of", is also understood as "consisting of", such as in "consisting of the steps of".

Methods for Obtaining Purified Recombinant Adeno-Associated Virus Particles

The invention relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition to a first step of anion-exchange chromatography on a chromatographic support wherein elution is performed by using a linear salt gradient and wherein the rAAV-containing fraction is collected, whereby a first rAAV enriched composition is provided;

c) submitting the first rAAV enriched composition at least once to a second step of anion-exchange chromatography on a chromatographic support wherein elution is performed by using a linear salt gradient and wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

According to some embodiments, the method does not include a step of treatment with detergents and/or nucleases, including DNAses.

According to some other embodiments the method does include a step of treatment with detergents and/or nucleases, including DNAses.

According to one embodiment, the rAAV particles belong to a AAV serotype selected in a group comprising AAV1, AAV2, AAV3, AAV4, AAV5, AAV8, AAV9, AAV10, and rhesus macaque-derived serotypes including AAVrh10, and mixtures thereof; in particular AAV4 and AAV5, and most preferably AAV5.

According to one embodiment, the rAAV particles consist of rAAV particles containing DNA comprising an expression cassette encoding human PDE6-beta or human RPE65.

Examples of expression cassettes which are suitable for the invention are further disclosed here after.

According to one particular embodiment, the rAAV particles consist of rAAV5 particles containing DNA comprising an expression cassette encoding human PDE6-beta.

According to said embodiment, the said expression cassette is of SEQ ID No 1.

According to one embodiment, the rAAV5 particles contain a DNA comprising SEQ ID No 2.

According to one particular embodiment, the rAAV particles consist of rAAV4 particles containing DNA comprising an expression cassette encoding human RPE65.

The terms "recombinant AAV virion", "rAAV virion", "AAV particle", "full capsids" and "full particles" are defined herein as an infectious, replication-defective virus including an AAV protein shell, encapsidating a heterologous nucleotide sequence of interest which is flanked on both sides by AAV ITRs. A rAAV virion is produced in a suitable host cell which has had sequences specifying an AAV plasmid, AAV helper functions and accessory functions introduced therein. In this manner, the host cell is rendered capable of encoding AAV polypeptides that are required for packaging the AAV plasmid (containing a recombinant nucleotide sequence of interest) into infectious recombinant virion particles for subsequent gene delivery.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.'

The term "host cell" denotes, for example, microorganisms, yeast cells, insect cells, and mammalian cells, that can be, or have been, used as transitory or permanent stable producer cell lines recipients of an AAV helper construct, an AAV plasmid, an accessory function plasmid, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The term "rAAV-containing clarified composition" encompasses any composition including rAAV particles, which is obtained after a step of depth-filtration of a starting material such as a cell lysate or a culture supernatant. A "rAAV-containing clarified composition" is distinct from a "rAAV enriched composition" and/or purified rAAV particles.

Thus, a "rAAV-containing clarified composition" may encompass any composition including rAAV particles which derives directly from a depth-filtered starting material such as a cell lysate or a culture supernatant, and which has not been further submitted to a step of enrichment and/or purification, including which has not been further submitted to a step of ion (e.g. cation)-exchange chromatography.

According to said embodiment, the invention relates to a method for obtaining purified recombinant Adeno-Associated Virus particles (rAAV), comprising the steps of:
 a) performing a depth filtration of a cell lysate and/or a culture supernatant, whereby a rAAV-containing clarified composition is provided;
 b) submitting the rAAV-containing clarified composition to a first step of anion-exchange chromatography on a chromatographic support wherein elution is performed by using a linear salt gradient and wherein the rAAV-containing fraction is collected, whereby a first rAAV enriched composition is provided;
 c) submitting the first rAAV enriched composition at least once to a second step of anion-exchange chromatography on a chromatographic support wherein elution is performed by using a linear salt gradient and wherein the rAAV-containing fraction is collected, whereby a second rAAV enriched composition is provided;
 d) submitting the second rAAV enriched composition to a step of tangential flow filtration, whereby purified recombinant Adeno-Associated Virus particles (rAAV) are provided.

According to another embodiment, the invention relates to a method for obtaining purified recombinant Adeno-Associated Virus particles (rAAV) of the invention, wherein the rAAV-containing clarified composition that is submitted to the first step of anion-exchange chromatography, is the composition obtained directly at the end of step a). Thus, according to said embodiment, steps a) and b) are consecutive steps.

By "consecutive step" is meant any step that comes after a first step, for which any inbetween step of chromatography step, in particular ion (cation)-exchange chromatography, is excluded. On the other hand, and unless stated otherwise, "consecutive steps" do not exclude buffer exchange and/or dilution steps, for the purpose of modifying buffer conditions (i.e. concentration of salt; pH) of said compositions.

According to an embodiment, the method of the invention does not comprise a cation-exchange chromatography step.

According to an embodiment, the method of the invention does not comprise an apatite chromatography step.

According to one preferred embodiment, the invention relates to a method for obtaining purified recombinant Adeno-Associated Virus particles (rAAV) of the invention, wherein anion-exchange chromatography steps are consecutive steps. Thus, according to said embodiment, steps b) and c) are consecutive steps.

According to another embodiment, steps c) and d) are consecutive.

According to another embodiment, steps b) and c) and d) are consecutive.

According to another embodiment, steps a) and b) and c) are consecutive.

According to another embodiment, steps a) and b) and c) and d) are consecutive.

According to said embodiment, the invention relates to a method for obtaining purified recombinant Adeno-Associated Virus particles (rAAV), comprising the steps of:
 a) performing a depth filtration of a starting material previously obtained from cells producing rAAV particles, the said starting material being selected in a group comprising a cell lysate and a culture supernatant, whereby a rAAV-containing clarified composition is provided;
 b) submitting the rAAV-containing clarified composition obtained at step a) to a first step of anion-exchange chromatography on a chromatographic support wherein elution is performed by using a linear salt gradient and wherein the rAAV-containing fraction is collected, whereby a first rAAV enriched composition is provided;
 c) submitting the first rAAV enriched composition obtained at step b) at least once to a second step of anion-exchange chromatography on a chromatographic support wherein elution is performed by using a linear salt gradient and wherein the rAAV-containing fraction is collected, whereby a second rAAV enriched composition is provided;

d) submitting the second rAAV enriched composition obtained at step c) to a step of tangential flow filtration, whereby purified recombinant Adeno-Associated Virus particles (rAAV) are provided.

According to another embodiment, steps a) and b) and c) and d) are consecutive and the starting material in step a) is directly obtained from a cell lysate or a culture supernatant.

According to said embodiment, the invention relates to a method for obtaining purified recombinant Adeno-Associated Virus particles (rAAV), comprising the steps of:

a) performing a depth filtration of a cell lysate and/or a culture supernatant, whereby a rAAV-containing clarified composition is provided;

b) submitting the rAAV-containing clarified composition obtained at step a) to a first step of anion-exchange chromatography on a chromatographic support wherein elution is performed by using a linear salt gradient and wherein the rAAV-containing fraction is collected, whereby a first rAAV enriched composition is provided;

c) submitting the first rAAV enriched composition obtained at step b) at least once to a second step of anion-exchange chromatography on a chromatographic support wherein elution is performed by using a linear salt gradient and wherein the rAAV-containing fraction is collected, whereby a second rAAV enriched composition is provided;

d) submitting the second rAAV enriched composition obtained at step c) to a step of tangential flow filtration, whereby purified recombinant Adeno-Associated Virus particles (rAAV) are provided.

The above-mentioned methods all include at least: 1) one step of depth filtration of a starting material; 2) a first step of anion-exchange chromatography; 3) a second step of anion-exchange chromatography; and 4) a step of tangential flow filtration. Each individual step will be further defined herebelow.

The inventors are also of the opinion that each additional step contributes to the scalability and high purity of the purified recombinant Adeno-Associated virus particles.

Depth Filtration

Depth filtration step allows for discarding a major part of contaminant DNA and proteins. This step renders possible the purification of rAAV particles through anion-exchange chromatography directly from a rAAV-containing clarified composition.

According to one embodiment, the starting material used at step a) is a cell lysate obtained by contacting a culture of cells producing rAAV particles with a composition comprising at least a detergent or a surfactant, and preferably a detergent.

According to one embodiment, the starting material used at step a) is a cell lysate obtained by contacting a culture of cells producing rAAV particles with a composition which may or may not comprise a detergent or a surfactant, but which is not treated with a nuclease such as a DNAse.

Examples of suitable detergents for cell lysis include Triton X-100, Triton X-114, NP-40, Brij-35, Brij-58, Tween 20, Tween 80, Octyl glucoside, Octyl thioglucoside, SDS, CHAPS and CHAPSO.

According to one preferred embodiment, step a) is performed by using a depth filter membrane comprising a layer of borosilicate glass microfibers and a layer of mixed esters of cellulose.

According to one exemplary embodiment, step a) is performed using a Polysep™ II (Millipore®) filter.

Anion-Exchange Chromatography

A number of suitable anion exchangers for use with the present invention are known and include without limitation, MACRO PREP Q (strong anion-exchanger available from BioRad, Hercules, Calif.); UNOSPHERE Q (strong anion-exchanger available from BioRad, Hercules, Calif.); POROS 50HQ (strong anion-exchanger available from Applied Biosystems, Foster City, Calif.); POROS 50D (weak anion-exchanger available from Applied Biosystems, Foster City, Calif.); POROS 50PI (weak anion-exchanger available from Applied Biosystems, Foster City, Calif.); SOURCE 30Q (strong anion-exchanger available from GE Healthcare, N.J.); DEAE SEPHAROSE (weak anion-exchanger available from GE Healthcare, Piscataway, N.J.); Q SEPHAROSE (strong anion-exchanger available from GE Healthcare, Piscataway, N.J.), Capto Q and Capto Adhere (GE Healthcare, N.J.).

According to some embodiments, the method for obtaining purified recombinant Adeno-Associated Virus particles (rAAV) comprises more than two anion-exchange chromatography steps, which includes in particular three or even four anion-chromatography steps. When the method comprises more than two anion-exchange chromatography steps, the aforementioned steps may be achieved on the same type of support or on different supports According to a preferred embodiment, the chromatographic support used at step b) is the same as the chromatographic support used at step c).

According to an exemplary embodiment, the chromatographic support at step b) and/or step c) is a monolithic chromatographic support.

Examples of suitable monolithic chromatographic supports are known in the Art, and include in a non-limitative manner the monolithic column CIMmultus® QA, CIM® QA, CIM DEAE and CIMmultus® DEAE (Bia Separations).

Chromatography monoliths are one-piece porous solids made of fused micrometer-sized globules of silica or an organic polymer that can be synthesized directly inside a chromatography tube. This makes this support very resistant and ready-to-use, with no package parameters variability.

Monoliths are homogenous columns with a continuous porous bed matrix, consisting of interconnected perfusion channels. These channels are relatively large (1-5 μm) by comparison to the typical pore sizes of packed-bed particle-based chromatography (5-100 nm). One benefit of this is that it increases the potential binding capacity of macromolecules such as virus because of high surface of accessibility. These supports generate low counter pressure even at high flow rates, and low shear rate.

By comparison to packed-bed columns, the improved mass transport of monolithic supports results in efficient separation of the macromolecules.

From a practical point of view, the use of these columns allows to work with a viral product (even when it is a cellular lysate) at high flow rate compared to packed-bed columns, with a high binding capacity and a good resolution, independent of the flow rate. The high resolution of these supports contributes to the reduction of the purification steps and the scalability of the whole process.

According to some embodiments, the method for obtaining purified recombinant Adeno-Associated Virus particles (rAAV), such as rAAV particles belonging to serotypes 4 or 5, comprises two or three anion-exchange chromatography steps on a monolithic chromatographic support, followed by a Tangential Flow Filtration (TFF) step as described further below.

The anion exchange column is first equilibrated using standard buffers and according to the manufacturer's specifications. For example, the column can be equilibrated with, e.g., a 5 to 50 mM, preferably 7-20 mM, such as 20 mM, Tris buffer. Sample is then loaded and two elution buffers are used, one low salt buffer and one high salt buffer.

Fractions are collected following a progressive mix of the low salt and high salt buffers, generating a salt gradient, and the eluted material is detected in the fractions using standard techniques, such as monitoring UV absorption at 260 and 280 nm. Using an anion exchanger, the protein peaks from the lower salt eluate contain AAV empty capsids and the higher salt fractions contain AAV particles.

In particular, on the anion exchange column, AAV particles can be further purified using an appropriate buffer at a pH of from about pH 5 to pH 12, preferably pH 6 to pH 10, and even more preferably pH 7 to pH 9.5, such as pH 7.1, 7.2, 7.3, 7.4-8.0, 8.1, 8.2, 8.3, 8.4, 8.5-9.0, 9.1, 9.2, 9.3, 9.4, 9.5, or any pH between the stated ranges.

Appropriate buffers for use with the anion exchange columns are well known in the art and are generally cationic or zwitterionic in nature. Such buffers include, without limitation, buffers with the following buffer ions: N-methylpiperazine; piperazine; Bis-Tris; Bis-Tris propane; Triethanolamine; Tris; N-methyldiethanolamine; 1,3-diaminopropane; ethanolamine; acetic acid, and the like. To elute the sample, the ionic strength of the starting buffer is increased using a salt, such as NaCl, KCl, sulfate, formate or acetate, at an appropriate pH.

Advantageously, all the buffers used during, before or after the anion-exchange chromatography comprise a non-ionic surfactant, for example Pluronic® F-68 (Gibco), in an amount ranging from 0.0001% to 0.1% (v/v) of the total volume of the buffer composition; which includes in an amount ranging from 0.0005% to 0.005% (v/v) of the total volume of the buffer composition; which includes about 0.001% (v/v) of the total volume of the buffer composition.

The use of a non-ionic surfactant, as defined above, and in the other steps, further contributes to the efficiency and scalability of the method. In particular, the use of a non-ionic surfactant, as defined above, prevents the aggregation or adherence of rAAV particles, before, during and after purification.

The nature of the resins used (i.e. strong or weak ion exchangers) and the conditions of salt concentration, buffer used, and pH, will vary on the AAV capsid variant (i.e. AAV capsid serotype or pseudotype). While the known AAV capsid variants all share features such as size and shape, they differ in fine details of molecular topology and surface charge distribution. Hence, while all capsid variants are expected to be amenable to purification by anion exchange chromatography, and relevant methods can be determined in a systematic manner using chromatography resin and buffer screening experiments, different conditions will be required for each AAV capsid variant to achieve efficient AAV particle purification. The determination of such conditions is readily apparent to the skilled artisan.

Advantageously, at the end of step a), the pH of the rAAV-containing clarified composition is adjusted at a basic pH so as to ensure optimal retention of the rAAV particles on the chromatographic support used at step b).

The pH used at step b) or c) for binding to the chromatographic support is preferably above the pH used during elution.

Preferably, the elution pH on the chromatographic support is adjusted depending on the rAAV particle that is purified. Elution at an optimal pH has the advantage of maintaining optimal infectivity of a given vector.

According to a particular embodiment, at the end of step a), the optimal pH of a rAAV-containing clarified composition, is adjusted at pH 8.

According to a particular embodiment, the optimal pH for binding of the rAAV particles to the chromatographic support at step b) or c) is above the optimal pH used of elution.

According to exemplary embodiments, the optimal pH for binding is of about 0.5 to 1 pH units higher than the pH used for elution.

Elution of rAAV particles from the chromatographic support at step b) or c), in particular elution of rAAV5 particles, can thus be adjusted at pH 8.

According to said embodiment, binding of rAAV particles to the chromatographic support can be adjusted at pH 8.5.

Appropriate buffers for use with the anion exchange columns are well known in the art and are generally cationic or zwitterionic in nature. Such buffers include, without limitation, buffers with the following buffer ions: N-methylpiperazine; piperazine; Bis-Tris; Bis-Tris propane; Triethanolamine; Tris; N-methyldiethanolamine; 1,3-diaminopropane; ethanolamine; acetic acid, and the like. To elute the sample, the ionic strength of the starting buffer is increased using a salt, such as NaCl, KCl, sulfate, formate or acetate, at an appropriate pH.

In particular, elution on the chromatographic support is performed by using a linear salt gradient. The salt may be selected from the group consisting of: NaCl, KCl, sulfate, formate and acetate; and preferably NaCl.

The anion-exchange chromatography may include a first step of treating the support, or anion-exchange column, with a lower salt concentration that what is generally used for the elution step. Such treatment may also be referred herein as a "first pre-elution" step.

Thus in one embodiment of the invention, the anion exchange column is first treated with a low salt concentration, e.g., 10-100 mM of salt, in particular 10-100 mM of NaCl, such as 10, 20, 25, 30, 35, 40, 45, 50, 55, 60, 65-100 mM, or any concentration within these ranges. For example the salt concentration in the "first pre-elution step" may initially correspond to the salt concentration of the buffer used for binding the rAAV particles to the column after loading.

Following initial treatment, the column is then treated with a higher salt concentration in order to elute impurities, such as a higher NaCl concentration, or with another buffer with a greater ionic strength. One example for use as the second buffer is a sodium acetate buffer or a Tris-based buffer. This additional step may also be referred herein as a "second pre-elution" step. In that case, one may take care that the salt concentration remains low enough to not elute the AAV particles from the column.

After additional impurities are eluted from the column, the AAV particles can then be recovered using a higher concentration of salt in the elution step.

The term "slope of the linear salt gradient" refers to the slope between two points (A,B) of the linear gradient, and depends both on the concentration of salt in the chromatography support and the column volume (CV) that is eluted over time, according to the following formula:

$$\text{slope}(A,B) = (\text{concentration of salt in } B\text{-concentration of salt in } A)/(\text{column volume in } B\text{-column volume in } A).$$

Thus, the slope of the linear salt gradient can be expressed in M/CV or in mM/CV, and is preferably a shallow salt gradient according to standard protocols.

According to one embodiment, the slope of the linear salt gradient at step c) is equal or inferior to the slope of the linear salt gradient at step b).

According to one embodiment, the slope of the linear salt gradient at step c) is of about half of the slope of the linear salt gradient at step b), or even less. Thus, the slope of the linear salt gradient at step c) may range from 1 to 70% of the slope of the linear salt gradient at step b), which includes 1, 2, 3, 4, 5, 6, 7, 8, 9, 10, 11, 12, 13, 14, 15, 16, 17, 18, 19, 20, 21 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70% of the slope of the linear salt gradient at step b).

According to one embodiment, the slope in step b) is equal or less than 0.1 M/CV, in particular ranging from 0,015 to 0.09 M/CV.

According to one embodiment, the slope in step c) is equal or less than 0.07 M/CV, in particular ranging from 0.01 to 0.06 M/CV.

Said gradients can be advantageously combined in the same process.

Thus, according to one embodiment, the slope of the linear salt gradient at step c) is equal or inferior to the slope of the linear salt gradient at step b), the slope at step b) being equal or less than 0.1 M/CV and the slope at step c) being equal or less than 0.07 M/CV.

According to one embodiment, the slope of the linear salt gradient of a N+1th anion-exchange chromatography step may be equal or inferior to the slope of the linear salt gradient of a Nth anion-exchange chromatography step, the slope of the Nth anion-exchange chromatography step being equal or less than 0.1 M/CV and the slope of the N+1th anion-exchange chromatography step being equal or less than 0.07 M/CV.

According to one exemplary embodiment, the elution in step b) is performed by using a NaCl salt gradient from 50 mM NaCl to 0.5 M NaCl over a gradient volume ranging from 5 to 30 times the column volumes, and preferably from 10 to 20 times the column volumes.

According to one exemplary embodiment, the elution in step c) is performed by using a NaCl salt gradient from 50 mM NaCl to 0.35 M NaCl over a gradient volume ranging from 5 to 30 times the column volumes, and preferably from 10 to 20 times the column volumes.

According to one embodiment, at step c), the first rAAV enriched composition is submitted to at least two anion-exchange chromatography steps, which includes two or more anion-exchange chromatography steps, which includes a plurality of anion-exchange chromatography steps. Thus, according to one particular embodiment, at step c), the first rAAV enriched composition may be submitted to two anion-exchange chromatography steps, which includes, two, three, or four or even more than four chromatography steps.

Advantageously, the method may include an additional step of dilution of the rAAV enriched composition before or after the at least one anion-exchange chromatography step. A step of dilution may be, for instance, in the form of a buffer exchange step.

According to said embodiment, each anion-exchange chromatography step that is performed at step c) may be identical or different. Preferably, each anion-exchange chromatography step that is performed at step c) is performed using a linear salt gradient having a slope equal or inferior to the slope of the linear salt gradient at step b).

If more than one anion-exchange chromatography step is performed in step c), the slope of the linear salt gradient for each individual anion-exchange chromatography step may be identical or different.

Thus, according to one embodiment, a first anion-exchange chromatography step can be performed by using a NaCl salt gradient from 50 mM NaCl to 0.35 M NaCl over a gradient volume ranging from 5 to 30 times the column volumes, and preferably from 10 to 20 times the column volumes. A second anion-exchange chromatography step is then performed using a NaCl salt gradient from 50 mM NaCl to 0.35 M NaCl over a gradient volume ranging from 5 to 30 times the column volumes, and preferably from 10 to 20 times the column volumes.

According to one preferred embodiment, at the end of step b), the first rAAV enriched composition is stored under a frozen form until its use for performing step c).

Tangential Flow Filtration and Subsequent Steps

Tangential Flow Filtration is a polishing step which allows to discard small-sized particle-related impurities through cycles of concentration and diafiltration through the pores of the filter. This polishing step has the other advantage of being suitable for changing the buffer of the eluted fractions and for concentrating the AAVs.

Tangential Flow Filtration is achieved preferably using, as a filter, a hollow fiber filter.

According to one embodiment, step d) is performed by using a filter membrane having a molecular weight cut-off value equal or inferior to 150 kDa, in particular ranging from 50 kDa to 150 kDa.

The man skilled in the Art will recognize that the molecular weight cut-off must be adjusted depending on the type of rAAV particle that is purified, on the conditions of the elution and, in particular, on the pH of elution.

According to some embodiment, salts and/or detergents and/or surfactants and/or nucleases can be added during, before or after the Tangential Flow Filtration, in particular during or before the Tangential Flow Filtration.

According to one embodiment, the method may further include a step of treatment with detergents and/or nucleases, including DNAses, during, before or after the Tangential Flow Filtration.

According to one embodiment, the purified recombinant Adeno-Associated Virus particles (rAAV) obtained at step c) or d) are submitted to an additional gradient, including a step of differential centrifugation, including density gradients, and in particular selected from: cesium chloride (CsCl) gradient centrifugation; iodixanol gradient centrifugation; sucrose gradient centrifugation.

According to one preferred embodiment, the method may further include an additional step of Tangential Flow Filtration after said additional gradient.

According to one embodiment, the purified recombinant Adeno-Associated Virus particles (rAAV) obtained at step d) are sterilized.

According to one embodiment, the purified recombinant Adeno-Associated Virus particles (rAAV) are submitted to a step of sterile filtration over a filter membrane having a pore size of 0.2 µm or less.

Thus, the invention also relates to purified rAAV particles obtained by performing a method as defined above.

Characterization of the Purified rAAV Particles

Advantageously, the above-mentioned method can be used for obtaining purified recombinant Adeno-Associated Virus particles (rAAV) which are suitable for gene therapy, and/or for preparing a medicament for gene therapy.

According to one preferred embodiment, said purified rAAV particles are suitable for use for gene therapy.

The purity of adeno-associated virus (AAV) particles preparations also has important implications for both safety and efficacy of clinical gene transfer.

The method used to purify an rAAV particle can dramatically influence the purity of the preparation in terms of the amount of host cell protein contamination and of ratio of full/total particles.

Vector particle concentration can be assessed by quantitative PCR (genome containing particles) or by ELISA (total vector particles), as shown in Example 1.

The purity of the preparation is most commonly assessed by sodium dodecyl sulfate-polyacrylamide gel electrophoresis (SDS-PAGE), as shown in Example 1.

Bands corresponding to the viral structural (capsid) proteins, VP1, VP2 and VP3 may be visualized after staining and their size and relative intensity assessed with respect to contaminating proteins. For reference, nucleic acids coding for VP1, VP2 and VP3 belonging to the AAV4 and AAV5 serotypes are of sequences SEQ ID No 10 to 15.

Nucleic acids coding for VP1, VP2, and VP3 belonging to the AAV4 serotype can be respectively of sequences SEQ ID No 10 to 12.

Nucleic acids coding for VP1, VP2, and VP3 belonging to the AAV5 serotype can be respectively of sequences SEQ ID No 13 to 15.

The above-mentioned sequences are given as references.

Thus, the term "purity" refers to the absence of general impurities. Purity is expressed as a percentage, and relates to the total amount of VP1, VP2 and VP3 proteins, in comparison to the total amount of detected proteins in a Coomassie Blue-stained Polyacrylamide gel.

The term "general impurities" refers to impurities which were present in the starting material but which are not considered as particle-related impurities. Thus, general impurities encompass impurities which are derived from the host cells but which are not AAV particles.

The term "particle-related impurities" refers to all types of AAV particles other than bona fide recombinant AAV particles. Particle-related impurities include empty AAV capsids (also referred to as "empties", or "empty particles", and AAV particles containing polynucleotide sequences other than the intended particle genome (also referred herein as "AAV-encapsidated nucleic acid impurities" or "AAV-encapsidated DNA impurities").

Residual DNA or Host Cell DNA can be present as contaminants in rAAV preparations. Because residual DNA can have negative effects, manufacturers must ensure that final products derived from host cells contain acceptable levels of residual DNA.

Residual DNA testing can be assessed by quantitative PCR, including real-time PCR, using the protocol described in Example 1. Residual DNA is expressed in ng per dose.

Preferably, residual DNA is determined by qPCR by determining the relative quantity of an E1A amplicon DNA in the composition, in comparison to a standard curve established with a known amount of E1A amplicon DNA.

A «dose» is defined as the volume of preparation which corresponds to $1*10^{12}$ vector genome (vg).

Advantageously, compositions of the invention can be further characterized by their ratio of empty rAAV particles/full rAAV particles.

The terms "empty capsid" and "empty particle" refer to an AAV virion that includes an AAV protein shell but that lacks in whole or part the polynucleotide construct comprising the heterologous nucleotide sequence of interest flanked on both sides by AAV ITRs. Accordingly, the empty capsid does not function to transfer the gene of interest into the host cell.

The ratio of empty rAAV particles/full rAAV particles can be assessed by SDSPAGE Gel, using the protocol described in Example 1.

Infectious particle concentration can also be assessed using the protocol of ICA described in Example 1.

Thus, a composition of the invention comprises at least one purified rAAV particle using either one of the above mentioned methods, and preferably has at least one of the following characteristics:
  a purity equal or superior to 90%, and preferably superior to 99%; or even 100%:
  an amount of residual cellular DNA equal or inferior to 50 ng per dose.

An amount of residual cellular DNA equal or inferior to 50 ng per dose includes equal or inferior to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, or 5 ng per dose.

In particular, a composition of the invention comprises at least one purified rAAV particle using either one of the above mentioned methods, and has the following characteristics:
  a purity equal or superior to 99%; or even 100%; and
  an amount of residual cellular DNA equal or inferior to 10 ng per dose.

Most preferably, the purity of the composition is superior to 99%, which includes a purity of 100%.

According to an exemplary embodiment, the composition is obtained directly from one of the above-mentioned methods.

According to an embodiment, a purified rAAV particle composition of the invention is a Saline Ocular Solution comprising rAAV particles purified according to the invention, optionally supplemented with a non-ionic surfactant.

Saline Ocular Solutions which are suitable for the invention may be obtained from BD Medical, such as for example BD Standard Solution or BD Aqueo Premium™.

According to said exemplary embodiment, the non-ionic surfactant is preferably Pluronic® F-68 (Gibco®).

The non-ionic surfactant (i.e. Pluronic® F-68) can be present in an amount ranging from 0.0001% to 0.1% (v/v) of the total volume of the composition; which includes in an amount ranging from 0.0005% to 0.005% (v/v) of the total volume of the composition; which includes about 0.001% (v/v) of the total volume of the composition.

Compositions of the invention, including compositions for administration and/or of use for gene therapy, as further described herebelow, are preferably sterile.

rAAV Particles for Use for Gene Therapy

The invention further relates to a method for obtaining purified recombinant Adeno-Associated Virus particles (rAAV), for use for gene therapy and/or for use for the preparation of a medicament suitable for gene therapy.

Advantageously, such rAAV particles and compositions thereof are also suitable, as such, for use for gene therapy, and/or for use for the preparation of a medicament suitable for gene therapy.

By "gene therapy" is meant the administration of a nucleic acid sequence to an individual, for treating and/or preventing and/or reducing the likelihood of the occurrence of a disease. Several approaches have been proposed in the Art. In view of the above, rAAV particles are used as vehicles for delivering said nucleic acid sequence to the individual to be treated.

One may replace a mutated gene that causes disease with a healthy copy of the gene.

One may inactivate ("knocking-out") a mutated gene that is functioning improperly.

One may introduce a new gene into the body for treating and/or preventing and/or reducing the likelihood of the occurrence of a disease.

The reported methods and plasmids are particularly efficient for use for preparing a medicament for eye-diseases, including sight loss, and more particularly rod-cone dystrophies due to rod-specific defects.

In particular, said disease may be selected from phosphodiesterase 6 (PDE6)-related diseases, including PDE6β-related diseases, and Retinal Pigment Epithelium-specific 65 kDa protein (RPE65)-related diseases.

RPE65-related diseases include Leber's congenital amaurosis and retinitis pigmentosa. PDE6-related diseases include Rod-cone Dystrophy, and retinitis pigmentosa The individual to be treated includes humans and non-human mammals.

AAV particles and compositions thereof may be administered topically or parenterally, which includes intraorbital and intraocular administration. Intraocular administration further includes intravitreal, subretinal and intracorneal administration.

Thus, compositions comprising said AAV particles are preferably suitable for topical or parenteral administration, which includes intraocular (preferably intravitreal and subretinal), and intracorneal administration.

rAAV particles of the invention preferably include an expression cassette encoding human PDE6β, or human RPE65 gene, respectively of sequences SEQ ID No 1 and 7, and as further described herebelow.

According to one preferred embodiment, a purified rAAV particle can be obtained by performing any one of the methods described herein. A purified rAAV particle composition comprises at least one of said purified rAAV particles. Purified rAAV particles and compositions thereof are suitable for use for gene therapy.

AAV Plasmids

AAV plasmids for producing said rAAV particles are further disclosed.

The construction of infectious recombinant AAV (rAAV) virions has been described. See e.g., U.S. Pat. Nos. 5,173,414 and 5,139,941; International Publication Numbers WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol, and Immunol. 158:97-129; and Kotin, R. M. (1994) Human Gene Therapy 5:793-801.

By an "AAV plasmid" is meant a plasmid derived from an adeno-associated virus serotype, including without limitation, AAV1, AAV2, AAV3, AAV4, AAV5, AAV6, AAV7 and AAV8 AAV9, AAV10, and rhesus macaque-derived serotypes including AAVrh10. AAV plasmids can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV plasmid is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. Also by an "AAV particle" is meant the protein shell or capsid, which provides an efficient vehicle for delivery of a nucleic acid to the nucleus of target cells.

Preferably, said AAV vector is derived from an adeno-associated virus selected from AAV4 or AAV5.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV plasmids.

The term "AAV helper construct" refers generally to a nucleic acid molecule that includes nucleotide sequences providing AAV functions deleted from an AAV plasmid which is to be used to produce a transducing plasmid for delivery of a nucleotide sequence of interest. AAV helper constructs are commonly used to provide transient or stable expression of AAV rep and/or cap genes to complement missing AAV functions that are necessary for AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See e.g., Samulski et al. (1989) J. Virol. 63:3822-3828; and McCarty et al. (1991) J. Virol. 65:2936-2945. A number of other plasmids have been described which encode Rep and/or Cap expression products. See e.g., U.S. Pat. Nos. 5,139,941 and 6,376,237.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells.

A "nucleic acid", "nucleotide sequence" or "polynucleotide sequence" refers to a DNA or RNA sequence. The term comprises sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil-dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-Dmannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, Buracil-5-oxyacetic acid methylester, uracil-5-oxyacetic acid, pseudouracil, queosine, 2-thiocytosine, and 2,6-diaminopurine.

A "coding sequence" or a sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

The term "heterologous" denotes sequences that are not normally joined together, and/or are not normally associated with a particular cell. Thus, a "heterologous" region of a nucleic acid construct or a plasmid is a segment of nucleic acid within or attached to another nucleic acid molecule that is not found in association with the other molecule in nature. The transgene comprising the heterologous nucleic acid can encode a number of useful products. These can include siRNA, antisense molecules, and miRNAs for example. Alternatively, transgenes can encode hormones and growth and differentiation factors.

AAV plasmids can be engineered to carry a heterologous nucleotide sequence of interest (e.g., a selected gene encoding a therapeutic protein, an antisense nucleic acid molecule, a ribozyme, a miRNA or the like) by deleting, in whole or in part, the internal portion of the AAV genome and inserting the DNA sequence of interest between the ITRs. The ITRs remain functional in such plasmids allowing replication and packaging of the rAAV containing the heterologous nucleotide sequence of interest. The heterologous nucleotide sequence is also typically linked to a promoter sequence capable of driving gene expression in the patient's target cells under the certain conditions. Termination signals, such as polyadenylation sites, can also be included in the plasmid.

The term "expression cassette" refers to a DNA nucleic acid sequence including at least one gene of interest, one open reading frame and a 3' untranslated region that, in eukaryotes, usually contains a polyadenylation site.

According to a general embodiment, an expression cassette according to the invention may thus comprise, or consist of, a DNA nucleic acid sequence having the general formula:

$$[5'ITR]-[\text{Gene of Interest}]-[PolyA]_z-[3'ITR]-$$

wherein [5'ITR] and [3'ITR] are inverted terminal repeats (ITR), wherein [Gene of Interest] is any gene coding for a protein of interest, wherein [PolyA] is a poly-adenylation signal with z being 0 or 1, and wherein each of [5'ITR], [Gene of Interest], [PolyA], and [3'ITR], can be optionally separated by one additional linker sequence.

In the sense of the invention, a "gene coding for a protein of interest" comprises at least one nucleic acid sequence coding for the protein of interest, and preferably at least one promoter.

Preferably the gene of interest is a nucleic acid coding for human PDE-6β or human RPE65.

According to one embodiment, the AAV plasmid comprises an expression cassette comprising a nucleic acid coding for human PDE-6B, of SEQ ID No 1.

According to one alternative embodiment, the AAV plasmid comprises an expression cassette comprising a nucleic acid coding for human RPE65, of SEQ ID No 7.

According to one particular embodiment, the AAV plasmid comprises a nucleic acid coding for human PDE6-B, of SEQ ID No 2.

According to one particular embodiment, the AAV plasmid comprises a nucleic acid coding for human RPE65, of SEQ ID No 7. According to one embodiment, the [5'ITR] and [3'ITR] are inverted terminal repeats derived from AAV-2, in particular inverted terminal repeats respectively of sequences SEQ ID No 3 and 4.

Advantageously, the AAV plasmid includes a polyadenylation site, an ITR derived from AAV2, and an expression cassette encoding human PDE6-beta.

Preferably, the expression of the human PDE6-beta gene is under the control of the promoter for Rhodopsine Kinase, preferably of sequence SEQ ID No 5.

According to an alternative embodiment, the AAV plasmid includes a polyadenylation site, an ITR derived from AAV2, and an expression cassette encoding human RPE65.

Preferably, the expression of the human RPE65 gene is under the control of the RPE65 promoter, preferably of sequence SEQ ID No 8.

According to one embodiment, the polyadenylation signal is derived from the Bovine Growth Hormone (bGH), preferably of sequence SEQ ID No 6.

The above-mentioned embodiments may be considered individually or in combination.

According to one most preferred embodiment, the AAV plasmid comprises an expression cassette comprising a nucleic coding for PDE6β as disclosed above and as illustrated in FIG. 1A.

Figure 1B:
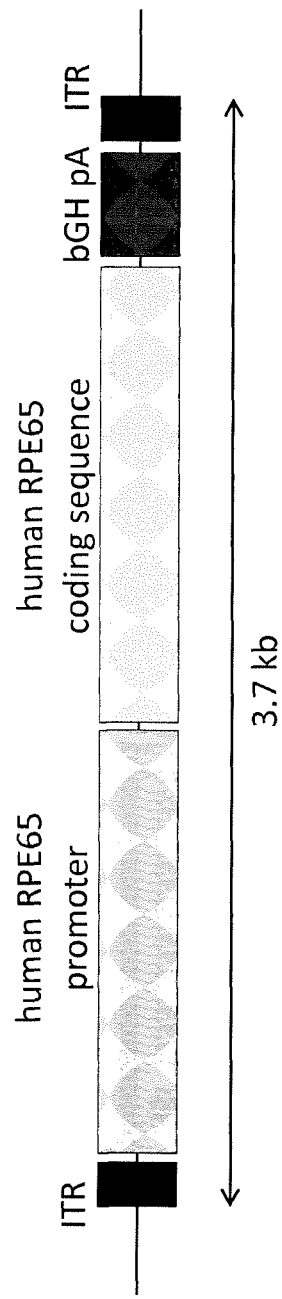
FIG. 1B: Cartography of the expression cassette of an AAV plasmid encoding human RPE65. The nucleic acid sequence coding for the human RPE65 protein is associated at its 5' end to a human RPE65 promoter and at its 3' end to a bovine growth hormone polyadenylation site (bGHpA), flanked by Inverted Terminal Repeat (ITR) sequences.
Figure 2:
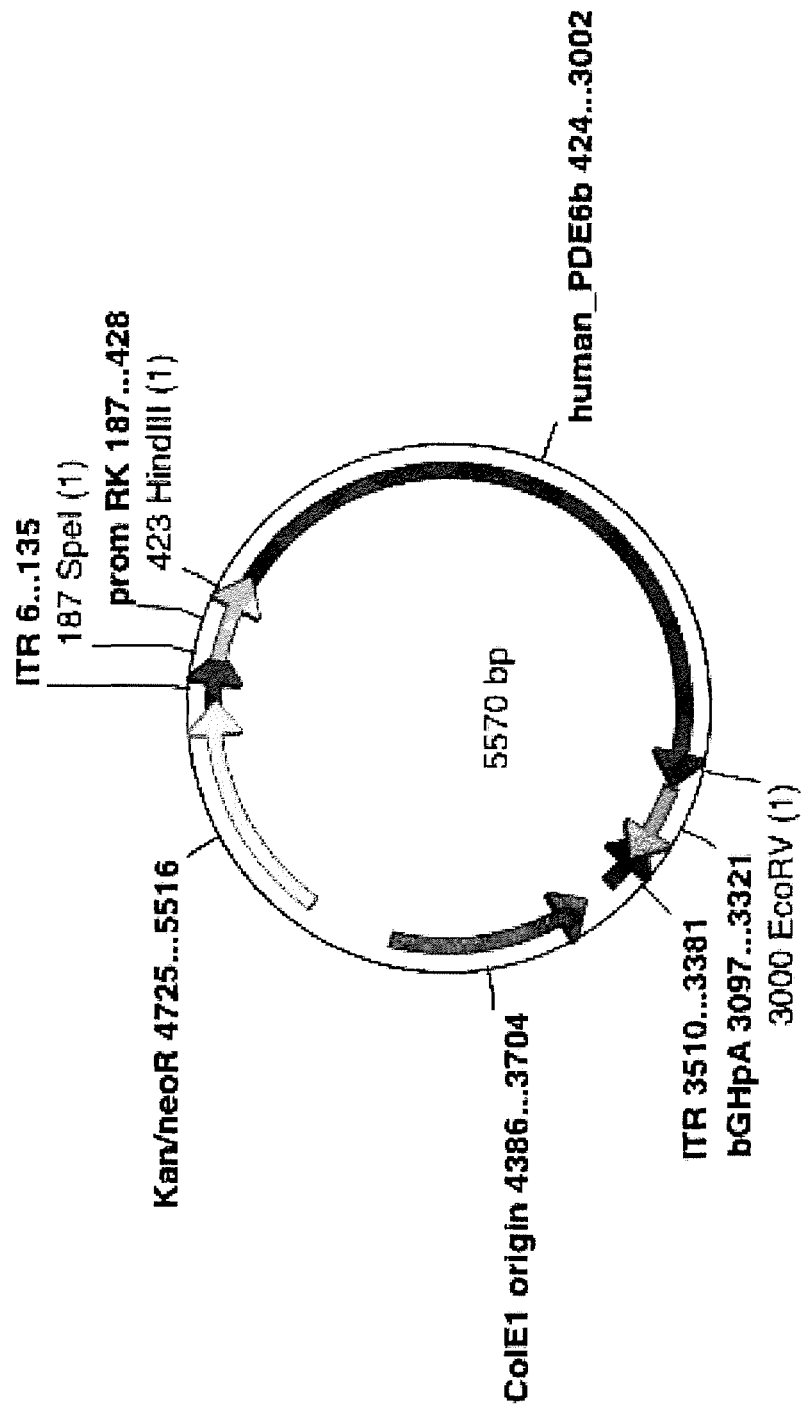
FIG. 2: Cartography of the whole AAV plasmid comprising the expression cassette encoding human PDE6β. The expression cassette is delimited by ITR sequences as defined in FIG. 1. Restriction sites are defined as EcoRV, SpeI and HindIII. The plasmid includes an additional Kanamycine (Kan/neoR) resistance marker and a Col1 origin. The directionality of sequences is indicated with arrows according to the standard nomenclature.

According to one alternative embodiment, the AAV plasmid comprises an expression cassette comprising a nucleic coding for RPE65 as disclosed above and as illustrated in FIG. 1B.

The invention further relates to a host cell which has been transfected with a AAV plasmid as defined above, and to a rAAV particle produced by said host cell.

The invention further relates to rAAV particles produced by the host cell, for use for gene therapy.

In particular, the invention further relates to rAAV particles selected from AAV1, AAV2, AAV3, AAV4, AAV5, AAV6, AAV7, AAV8, AAV9, AAV10, and rhesus macaque-derived serotypes including AAVrh10. Preferably rAAV particles are selected from rAAV particles belonging to the AAV4 and/or AAV5 serotype.

In particular, the invention relates to rAAV5 particles containing DNA comprising an expression cassette encoding human PDE6-beta as defined above.

EXAMPLES

Example 1: Two-Step Anion-Exchange Chromatography for Purifying rAAV5 Particles A. Material & Methods A1. Harvest of the Cell Lysate.

Transfected cells are harvested at 96+/−5 hours post transfection by rapping the CellStacks 10 (CS10) on all sides. The entire suspension is transferred in a BioProcess Container (BPC). A major part of the viral particle is released in the supernatant.

A2. Clarification of the Cell Lysate.

The entire suspension obtained with 20 CS10 is filtered through a Millipore depth filter Polysep II 1/0.5 μm-30"—at 1200 mL/min flow rate, to discard the cell debris. At the end of the filtration step, the filtration unit is emptied by pushing with air. The filtration unit is rinsed with 15 L of buffer Tris 20 mM, $MgCl_2$ 2 mM, $CaCl_2$) 1 mM, pH 9, which is combined with the filtered lysate. This is the clarified lysate. During this step a great part of DNA and soluble proteins are discarded as well. To adjust the parametres (pH and conductivity) to the right binding conditions, the clarified lysate is diluted with 30 L of buffer Tris 20 mM, $MgCl_2$ 2 mM, $CaCl_2$) 1 mM, pH 8.5. The critical parametres (pH and conductivity) are controlled, in comparison of the injection buffer (pH 8.5, conductivity 6+/−1 mS).

These conditions were determined to be optimal for the binding of the AAV5 vector to this column A3. $1^{st}$ Anion-Exchange Chromatography Purification Step.

This step is realised with an Akta Pilot (GE Healthcare) controlled by a Unicorn software. 67 L of diluted product in a 100 L BPC are injected at 400 mL/min flow rate through a Monolith CIMmultus QA-800 mL-equilibrated with buffer 1: Tris 20 mM, NaCl 50 mM, MgCl2 2 mM, CaCl2 1 mM, pH 8.5. During this step the AAV and some impurities bind to the column. A major amount of impurities does not bind to the column and is discarded in the flowthrough. To wash the unspecific bound particles, the column is then rinsed with 15 CV (Column Volume) of buffer 1. The elution step is a NaCl salt gradient with a very shallow slope which is the result of mixing buffer 2 (Tris 20 mM, NaCl 50 mM, $MgCl_2$ 2 mM, $CaCl_2$) 1 mM, pH 8.0) with buffer 3 (Tris 20 mM, NaCl 1 M, $MgCl_2$ 2 mM, $CaCl_2$) 1 mM, pH 8.0). The slope of the gradient is suitable for obtaining 50% of buffer 3 in 15 CV. The slow increase of salt allows to elute gradually AAV and other impurities.

The elution of species bound to the column (including AAV) is made at pH of 8.0, in opposition to the binding at pH 8, 5. This pH was adjusted to keep the infectiosity of the vector during the freezing storage between purification steps (pH 8.5 was particularly deleterious for AAV5 infectiosity).

Eluted fractions are collected in polypropylene bottles and stored at <−65° C., or even <−80° C., until the next step (usually around one week). During this time the collected fractions are screened for the presence of viral particles.

A4. $2^{nd}$ Anion-Exchange Chromatography Purification Step.

The $2^{nd}$ chromatography step is similar to the first one except that the gradient is more shallow. The effect of this step is to further separate AAV from impurities.

Selected fractions from the $1^{st}$ chromatographic step, containing AAV particles are pooled (1.5 to 2 L). To adjust the parametres (pH and conductivity) to the right binding conditions the pool of fractions is diluted with 4 L of Tris 20 mM, $MgCl_2$ 2 mM, $CaCl_2$) 1 mM, pH 8.5 and 21 of Tris 20 mM, NaCl 50 mM, $MgCl_2$ 2 mM, $CaCl_2$) 1 mM, pH 8.5. The parameters are controlled in comparison to the buffer 1. All the steps of the $1^{st}$ chromatographic separation are repeated with the same column monolith CIMmultus QA-800 mL, except that the elution is a gradient to obtain 30% of buffer 3 in 15 CV. Eluted fractions are collected in polypropylene bottles and stored at <−65° C., or even <−80° C., until the next purification step (usually around 2 weeks). During this time the collected fractions are screened for the presence of viral particles.

A5. Tangential Flow Filtration (TFF).

Selected fractions from the $2^{nd}$ chromatographic step containing AAV are pooled (around 1 L). TFF is done using a mPES hollow fibre with a cut off of 100 KDa. AAV is diafiltered and concentrated against Saline Ocular Solution (SSO).

The pooled fractions are first slightly concentrated, diafiltered against 10 volumes of buffer and finally concentrated to reach the expected concentration. TFF allows to discard the remaining small size impurities as well as to formulate the viral vector in the right buffer for injection and to concentrate to the right level. The filtered purified and concentrated viral vector is stored at <−65° C., or even <−80° C. until titration.

A6. Sterile Filtration.

AAV is diluted with SOS (Saline Ocular Solution) to obtain the precise concentration necessary for the injection to patients and sterile filtered with a 0.2 μm PES filter before to be aliquoted in final container according to the expected volume. Doses are stored at <−65° C., or even <−80° C. until injection.

A7. Vector Genome Concentration by qPCR (Vg/mL)

This method consists in the determination of genome-containing particles by quantitative PCR (qPCR) targeting the expression cassette of the transgene (the transgene, the poly(A), the ITR or the promoter). The rAAV samples are first digested with DNase in order to eliminate non-encapsidated DNA. Afterwards, a Proteinase K treatment degrades AAV capsids and releases the viral DNA for the subsequent qPCR quantification.

The vector plasmid containing the targeted amplicon is used to generate the standard curve for the qPCR. This plasmid is linearized by restriction endonuclease digestion, aliquoted and stored at ≤−18° C. to ensure stability and reproducibility of the standard curve in each assay.

The calculation of $1^e10$ copies of amplicon is based on the following formula:

$$\text{Quantity of DNA (g)} = (660 \times \text{plasmid size (bp)} \times 1^e 10 \text{ copies})/(6.02 \times 10^{e}23)$$

The relative quantity of vector genome DNA is assigned by extrapolation of copy number per reaction from the standard curve containing a known amount of amplicon DNA.

The results are reported in vector genome per mL.

A8. Infectious Particles Concentration by ICA (Ip/mL)

The Infectious Center Assay (ICA) allows the quantification of infectious particles in a rAAV lot. This assay involves the infection of a permissive cell line stably carrying the AAV2 rep and cap sequences (HeLaRC32, ATCC CRL-2972) with increasing serial dilutions of the rAAV vector and with wild-type Adenovirus (type 5). Thus, infectious rAAV particles entering into the cells will be able to replicate. The replication events are then detected by chemiluminescence and quantified following hybridization with a transgene specific probe (Salvetti et al., Hum Gene Ther, 1998).

Twenty-six hours post-infection, the cells are harvested, lysed and blotted on a nylon membrane. An hybridization is performed with a specific transgene probe labeled with fluorescein. The signal is then amplified with an anti-fluorescein antibody coupled with Alkaline Phosphatase and detected by chemiluminescence.

Finally, the replication events are quantified by dot counting after revelation on a radiographic film.

A9. Vector Particles Concentration by ELISA (vp/mL)

The total AAV5 capsid concentration of rAAV is determined by a commercially available sandwich ELISA method from Progen (Cat. #PRAAV5)

A unique microtiter plate enzyme immunoassay is used for the quantitation of recombinant AAV5 virions or assembled and intact empty capsids of Adeno-Associated Virus 5. The capture-antibody detects a conformational epitope not present on unassembled capsid proteins.

The drug product is first diluted and applied to wells coated with the monoclonal antibody. Captured AAV5 particles are then detected by addition of a biotin-conjugated monoclonal antibody, followed by a streptavidin peroxidase conjugate and the TMB chromogenic substrate (TetraMéthylBenzidine). The resulting color reaction product, which is proportional to specifically bound intact capsid particles, is measured photometrically at 450-nm.

The concentration of AAV5 capsids present in the sample is extrapolated from a standard curve, corrected for the appropriate dilution factor, and reported in vector particles per mL.

A10. Vector Capsid Purity and Identity by SDS-PAGE and Coomassie Blue Staining.

The SDS-PAGE method is an electrophoresis in a polyacrylamide gel in denaturing conditions that separates the proteins and the other components of the sample depending on their molecular weight and their charges.

After electrophoresis, the gel is stained with Coomassie blue (Imperial Protein Stain) in order to quantify only the proteins in the samples. The protein identity of the rAAV is confirmed by the presence of the three capsids proteins of AAV called VP1, VP2 and VP3. The protein purity of rAAV is calculated as a relative amount of capsid proteins compared to the total amount of proteins present in the sample.

The electrophoresis gel is analyzed after Coomassie blue staining by a luminescent image analyzer with a CCD camera. Each band of protein is detected as a peak and the signal is integrated by the analyzer. The area of each peak is then calculated; a 100% pure product contains only the three VP1, VP2 and VP3 protein bands.

A11. Vector Particles Quantification by SDS-PAGE and Silver Staining

The silver staining, based on the methodology of Heukeshoven and Dernick (Heukeshoven and Dernick Electrophoresis, 1985), allows the detection of proteins and nucleic acids separated by polyacrylamide gel electrophoresis.

The sample is loaded on the same gel as the rAAV used for the standard curve. The standard curve is generated using a referent rAAV lot, produced and characterized the same way than the rAAV8RSM (Ayuso et al, Hum Gene Ther. 2014), and containing 100% full particles.

After electrophoresis, the gel is analyzed using an image analyzer with a CCD camera, and the signal of the band corresponding to VP3 is integrated for each lane. The quantity of total capsids present in the sample is extrapolated from the standard curve, and reported in particles per mL.

The ratio full/total particles is based on the following calculation: Titer in vector genome per mL/titer in particles per mL.

For reference: Simplified method for silver staining of proteins in polyacrylamide gels and the mechanism of silver staining. (Electrophoresis 6 (1985) 103-112, Heukeshoven, J. and Dernick, R.) & Manufacturing and Characterization of a recombinant associated virus type 8 reference standard material, Ayuso et al, (Hum Gene Ther. 2014 Oct. 2).

A12. Residual Host Cell DNA by qPCR (Albumin and E1A from HEK 293 Cells)

The residual Human Host Cell DNA is determined using a real-time quantitative PCR method targeting the human albumin or the adenovirus type 5 E1A genes.

A plasmid containing the specific amplicons (albumin and E1A) is used to generate the standard curve for the qPCR. This plasmid is linearized by restriction endonuclease digestion, filled and stored at $\leq-18°$ C. to ensure stability and reproducibility of the standard curve in each assay. The calculation of $1^e10$ copies of albumin gene sequence is based on the following calculation:

Quantity of DNA (g)=(660×plasmid size (bp)×1e10 copies)/6.02×10$^e$23.

The relative quantity of albumin or E1A amplicon DNA is assigned by extrapolation of copy number per reaction from the standard curve containing a known amount of albumin or E1A amplicon DNA.

A second standard curve is performed with genomic DNA from HEK293 cell line, from 50 µg to 5 ng per well. This standard curve indicates the correlation between the amount of albumin or E1A copy and the corresponding amount in ng of HEK293 DNA.

B. Results

B1. Development in Large Scale Batches

Figure 3A:
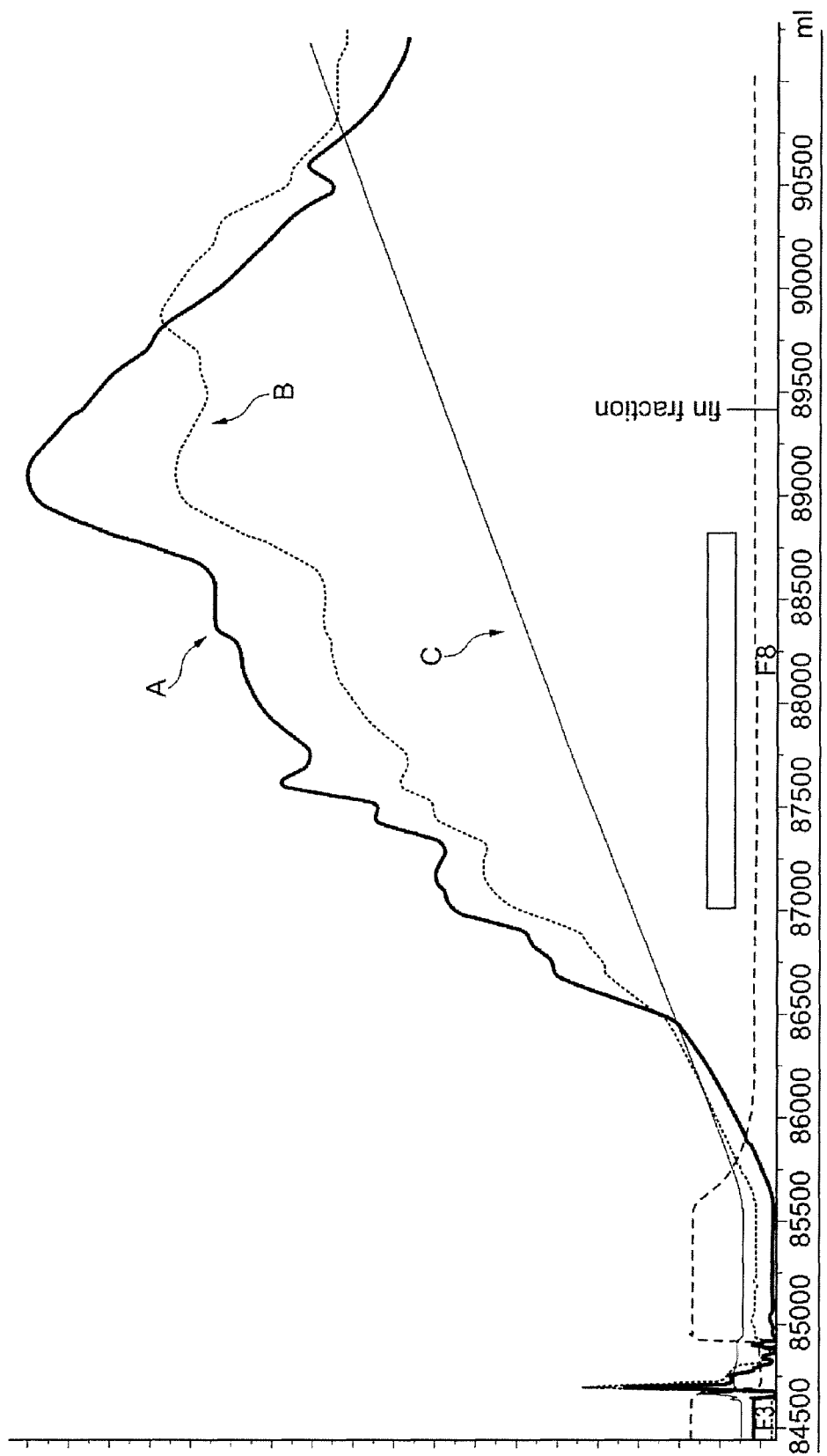
FIG. 3A: Chromatography profile of the elution phase corresponding to the $1^{st}$ Anion-Exchange Chromatography step from a rAAV5-containing preparation. Curves represent Absorbance (left axis in mAU) at 280 nm (A line) and 260 nm (B line). Line C represents the conductivity in mS/cm. Empty squares show where the AAVs are eluted.
Figure 3B:
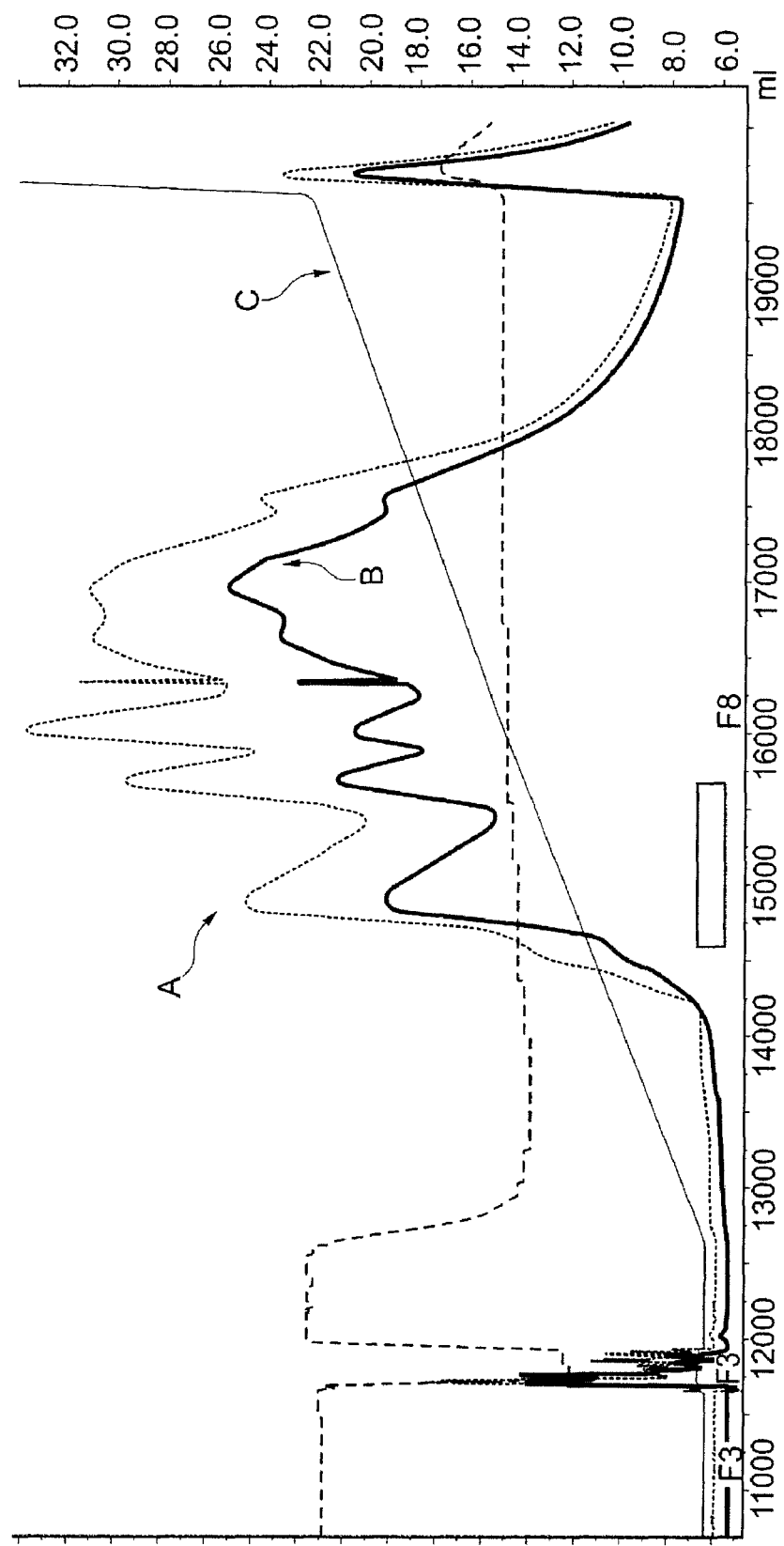
FIG. 3B: Chromatography profile of the elution phase corresponding to the $2^{nd}$ Anion-Exchange Chromatography step from a rAAV5-containing preparation. Curves represent Absorbance (left axis in mAU) at 280 nm (A line) and 260 nm (B line). Line C represents the conductivity in mS/cm (right axis). Empty squares show where the AAVs-containing fractions are eluted.

FIGS. 3A and 3B illustrate the elution profile of a clarified supernatant containing AAV5 particles, respectively from a first step of anion-exchange chromatography (see FIG. 3A), and from a second step of anion-exchange chromatography (see FIG. 3B).

The purification method is achieved at a large scale (22 L). Titration of the vector genome at each step and characterization of the final product are established according to the abovementioned protocols and summarized in the following tables:

TABLE 1 titration of the vector genome from two large scale (22 L) batches

|  | $1^{st}$ batch | $2^{nd}$ batch |
|---|---|---|
| Harvest | $2.1\ 10^{15}$ | $1.1\ 10^{15}$ |
| Depth filtration | $8.7\ 10^{14}$ | $6.2\ 10^{14}$ |
| $1^{st}$ Anion-exchange column | $6.7\ 10^{14}$ | $3.5\ 10^{14}$ |
| $2^{nd}$ Anion-exchange column | $5.0\ 10^{14}$ | $2.6\ 10^{14}$ |
| Tangential Flow Filtration | $3.3\ 10^{14}$ | $2.3\ 10^{14}$ |
| Final Product | $3.3\ 10^{14}$ | $1.9\ 10^{14}$ |
| Total Yield | 16% | 17% |
| Final concentration | $1.8\ 10^{13}$/mL | $1.6\ 10^{12}$/mL |

TABLE 2 characterization of the final product

|  | $1^{st}$ batch | $2^{nd}$ batch |
|---|---|---|
| Titer (vg/mL) | $1.8\ 10^{13}$ | $1.6\ 10^{12}$ |
| Infectious Titer (pi/mL) | $7.2\ 10^{9}$ | $9.3\ 10^{8}$ |
| Ratio vg/pi | 2500 | 1700 |
| Purity (Proteins) | 100% (>99%) | 100% (>99%) |
| resDNA (Alb) ng/dose* | 0.15 | <1.4 |
| resDNA (E1A) ng/dose* | 4.2 | 4.5 |

*where a dose is 1
*$10^{12}$ vector genome (vg)

Conclusion: this protocol is reproducible and efficient for purifying clinical-grade AAV5 preparations from clarified supernatants at a large scale, and in good yields. Advantageously, the $2^{nd}$ consecutive anion-exchange column chromatography step only impacts moderately the titer of the vector genome.

B2. Application to Different AAV5 Viral Vectors

This process was applied to different AAV5 viral vectors, containing different transgenes.

Two small scale batches of 2.2 Liters were produced and purified for each AAV5 (3 different transgenes), in the same conditions as those described above in the Material & Methods section.

The results are summarized in table 3 below. All vectors are pure at >90%.

TABLE 3

Results (vector genome) obtained from 2 small scale batches for each vector

|  | Batch 1 PDE6β | Batch 2 PDE6β | Batch 1 Gene 2 | Batch 2 Gene 2 | Batch 1 Gene 3 | Batch 2 Gene 3 |
|---|---|---|---|---|---|---|
| Harvest | $9.0\ 10^{13}$ | $2.9\ 10^{14}$ | $1.1\ 10^{14}$ | $9.0\ 10^{13}$ | $1.7\ 10^{14}$ | $3.0\ 10^{14}$ |
| Final Product | $1.8\ 10^{13}$ | $4.3\ 10^{13}$ | $2.9\ 10^{13}$ | $1.4\ 10^{13}$ | $2.4\ 10^{13}$ | $2.8\ 10^{13}$ |
| Total Yield | 20% | 15% | 26% | 16% | 14% | 9% |
| Final concentration | $1.3\ 10^{12}$/mL | $7.5\ 10^{12}$/mL | $9.1\ 10^{12}$/mL | $4.3\ 10^{12}$/mL | $1.3\ 10^{12}$/mL | $1.5\ 10^{12}$/mL |

Conclusion: the robustness of the process makes it applicable to different AAV5 serotypes containing different transgenes with the same quality of final product.

Example 2: Two-Step Anion-Exchange Chromatography for Purifying rAAV4 Particles

A. Material & Methods

A1. Harvest of the Cell Lysate.

Transfected cells are harvested at 97 hours post transfection by rapping the CellStack (CS10) on all sides. The entire suspension is treated with Triton X-100 (1% v/v final) during one hour at room temperature to release particles from the cells (80% of AAV in the supernatant before treatment, 98% after treatment) and to facilitate the step of depth filtration (better recovery of the depth filtration step).

A2. Clarification of the Cell Lysate.

The cells suspension obtained is filtered through a Millipore depth filter Polysep II 1/0.5 μm-2"—at 90 mL/min flow rate, to discard the cell debris. At the end of the filtration step, the filtration unit is emptied by pushing with air. The filtration unit is rinsed with 600 mL of buffer Tris 20 mM, $MgCl_2$ 2 mM, $CaCl_2$) 1 mM, pH 8, which is combined with the filtered lysate. This is the clarified lysate. During this step a great part of DNA and soluble proteins are discarded as well. To adjust the parametres (pH and conductivity) to the right binding conditions, the clarified lysate is diluted with 1.4 L of buffer Tris 20 mM, $MgCl_2$ 2 mM, $CaCl_2$) 1 mM, pH 8. The critical parametres (pH and conductivity) are controlled, in comparison of the injection buffer (pH 8.0, conductivity 6+/−1 mS).

A3. $1^{st}$ Anion-Exchange Chromatography Purification Step.

This step is realised with an Akta Pilot (GE Healthcare) controlled by a Unicorn software. 3 L of diluted product are injected at 100 mL/min flow rate through a Monolith CIMmultus QA-80 mL-equilibrated with buffer 1: Tris 20 mM, NaCl 50 mM, $MgCl_2$ 2 mM, CaCl2 1 mM, pH 8. During this step the AAV and some impurities bind to the column. A major amount of impurities does not bind to the column and is discarded in the flowthrough. To wash the unspecific bound particles, the column is then rinsed with buffer 1 until a stable level of absorbance. The elution step is a NaCl salt gradient with a very shallow slope that is the result of mixing buffer 1 with buffer 2 (Tris 20 mM, NaCl 350 mM, $MgCl_2$ 2 mM, $CaCl_2$) 1 mM, pH 8). The elution is realised to obtain 100% of buffer 2 in 10 CV. The slow increase of salt allows to elute gradually AAV and other impurities.

Eluted fractions are collected in polypropylene tubes and stored at <−80° C. until the next step. The collected fractions are screened for the presence of viral particles.

A4. $2^{nd}$ Anion-Exchange Chromatography Purification Step.

The $2^{nd}$ chromatography step is similar to the first one except that the gradient is more shallow. The effect of this step is to further separate AAV from impurities.

Selected fractions from the $1^{st}$ chromatographic step, containing AAV particles are pooled (350 mL). To adjust the parameters (pH and conductivity) to the right binding conditions the pool of fractions is diluted with 900 mL of Tris 20 mM, $MgCl_2$ 2 mM, $CaCl_2$) 1 mM, pH 8. The parameters are controlled in comparison to the buffer 1. All the steps of the $1^{st}$ chromatographic separation are repeated with the same column monolith CIMmultus QA-80 mL, except that the elution is a gradient to obtain 100% of buffer 2 in 40 CV. Eluted fractions are collected in polypropylene bottles and stored at <−80° C. until the next purification step. The collected fractions are screened for the presence of viral particles.

A5. Tangential Flow Filtration (TFF).

Selected fractions from the 2$^{nd}$ chromatographic step containing AAV are pooled (around 700 mL). TFF is done using a mPES hollow fiber with a cut off of 50 KDa. AAV is diafiltered and concentrated against Saline Ocular Solution (SOS).

The pooled fractions are first slightly concentrated, diafiltered against 10 volumes of buffer and finally concentrated to reach the expected concentration. The filtered purified and concentrated viral vector is stored at <−80° C. until titration.

B. Results

The results obtained for AAV4 of this example are summarized in the table 4 below.

Titration of the vector genome at each step is established according to the abovementioned protocol.

TABLE 4

| titration of the vector genome | |
|---|---|
| Harvest | 5 10$^{13}$ |
| Depth filtration | 5.2 10$^{13}$ |
| 1$^{st}$ Anion-exchange column | 4 10$^{13}$ |
| 2$^{nd}$ Anion-exchange column | 2.6 10$^{13}$ |
| Tangential Flow Filtration | 9.6 10$^{12}$ |
| Total Yield | 19% |

SEQUENCE LISTING

| | |
|---|---|
| SEQ ID No 1 | Expression cassette encoding human PDE6β |
| SEQ ID No 2 | Nucleic acid coding for human PDE6-β |
| SEQ ID No 3 | [5'TTR] inverted terminal repeat derived from AAV-2 |
| SEQ ID No 4 | [3'TTR] inverted terminal repeat derived from AAV-2 |
| SEQ ID No 5 | Promoter for Rhodopsine Kinase |
| SEQ ID No 6 | [PolyA] signal derived from the Bovine Growth Hormone (bGH) |
| SEQ ID No 7 | Expression cassette of human RPE65 |
| SEQ ID No 8 | Human RPE65 gene promoter |
| SEQ ID No 9 | Nucleic acid coding for human RPE65 |
| SEQ ID No 10 | AAV-4 VP1 coding sequence (2205 nt) |
| SEQ ID No 11 | AAV-4 VP2 coding sequence (409-2205 of VP1) |
| SEQ ID No 12 | AAV-4 VP3 coding sequence (589-2205 of VP1) |
| SEQ ID No 13 | AAV-5 VP1 coding sequence (2175 nt) |
| SEQ ID No 14 | AAV-5 VP2 coding sequence (409-2175 of VP1) |
| SEQ ID No 15 | AAV-5 VP3 coding sequence (577-2175 of VP1) |

The invention claimed is:

1. A method for obtaining purified recombinant Adeno-Associated Virus (rAAV) particles, comprising the steps of:
  a) performing a depth filtration of a starting material previously obtained from cells producing rAAV particles, the said starting material being a cell lysate or a culture supernatant, whereby a rAAV-containing clarified composition is provided;
  b) submitting the rAAV-containing clarified composition to a first step of anion-exchange chromatography on a chromatographic support, wherein elution is performed by using a linear salt gradient and wherein the rAAV-containing fraction is collected, whereby a first rAAV enriched composition is provided;
  c) submitting the first rAAV enriched composition at least once to a second step of anion-exchange chromatography on a chromatographic support wherein elution is performed by using a linear salt gradient and wherein the rAAV-containing fraction is collected, whereby a second rAAV enriched composition is provided;
  d) submitting the second rAAV enriched composition to a step of tangential flow filtration, whereby purified recombinant Adeno-Associated Virus particles (rAAV) are provided;
  wherein said rAAV particles belong to an AAV5 capsid serotype and
  wherein the purified rAAV particles have an amount of residual host cell DNA equal or inferior to 50 ng per dose of $10^{12}$ vector genomes (vg) of the rAAV particles that belong to the AAV5 capsid serotype.

2. The method according to claim 1, wherein at the end of step a), the pH of the rAAV-containing clarified composition is adjusted at a basic pH so as to ensure optimal retention of the rAAV particles on the chromatographic support used at step b).

3. The method according to claim 1, wherein the chromatographic support at step b) or step c) is a monolithic chromatographic support.

4. The method according to claim 1, wherein step d) is performed by using a filter membrane having a molecular weight cut-off value ranging from 50 kDa to 150 kDa.

5. The method according to claim 1, wherein the rAAV particle contains DNA comprising an expression cassette encoding human phosphodiesterase 6B-beta.

6. The method according to claim 1, wherein the purified rAAV particles have a purity of at least 90%.

7. The method according to claim 1, wherein the final yield of purified rAAV particles is equal or superior to 10%.

8. The method according to claim 5, wherein the final yield of purified rAAV particles is equal or superior to 15%.

* * * * *

```
                        SEQUENCE LISTING

<160> NUMBER OF SEQ ID NOS: 15

<210> SEQ ID NO 1
<211> LENGTH: 3505
<212> TYPE: DNA
<213> ORGANISM: Artificial Sequence
<220> FEATURE:
<223> OTHER INFORMATION: Synthetic Expression cassette encoding human
      PDE6beta

<400> SEQUENCE: 1
ctgcgcgctc gctcgctcac tgaggccgcc cgggcaaagc ccgggcgtcg ggcgaccttt      60
ggccgggcgg cctcagtgag cgagcgagcg cgcagagagg gagtggccaa ctccatcact     120
aggggttcct tgtagttaat gattaacccg ccatgctact tatctacgac attgattatt     180
gactagtccg gatccaagct cagatctcga gttgggcccc agaagcctgg tggttgtttg     240
tccttctcag gggaaaagtg aggcggcccc ttggaggaag gggccgggca gaatgatcta     300
atcggattcc aagcagctca ggggattgtc tttttctagc accttcttgc cactcctaag     360
cgtcctccgt gaccccggct gggatttagc ctggtgctgt gtcagcccg ggtcgacaag      420 cttggatcca tgagcctcag tgaggagcag gcccggagct ttctggacca gaaccccgat     480
tttgcccgcc agtactttgg gaagaaactg agccctgaga atgtggccgc ggcctgcgag     540
gacgggtgcc cgccggactg cgacagcctc cgggacctct gccaggtgga ggagagcacg     600
gcgctgctgg agctggtgca ggatatgcag gagagcatca acatggagcg cgtggtcttc     660
aaggtcctgc ggcgcctctg caccctcctg caggccgacc gctgcagcct cttcatgtac     720
cgccagcgca acgcgtggc cgagctggcc accaggcttt tcagcgtgca gccggacagc     780
gtcctggagg actgcctggt gcccccgac tccgagatcg tcttcccact ggacatcggg     840
gtcgtgggcc acgtggctca gaccaaaaag atggtgaacg tcgaggacgt ggccgagtgc     900
cctcacttca gctcatttgc tgacgagctc actgactaca gacaaagaa tatgctggcc      960 acacccatca tgaatggcaa agacgtcgtg gcggtgatca tggcagtgaa caagctcaac    1020
```

```
ggcccattct tcaccagcga agacgaagat gtgttcttga agtacctgaa ttttgccacg   1080
ttgtacctga agatctatca cctgagctac ctccacaact gcgagacgcg ccgcggccag   1140
gtgctgctgt ggtcggccaa caaggtgttt gaggagctga cggacatcga gaggcagttc   1200
cacaaggcct tctacacggt gcgggcctac ctcaactgcg agcggtactc cgtgggcctc   1260
ctggacatga ccaaggagaa ggaattttt gacgtgtggt ctgtgctgat gggagagtcc   1320
cagccgtact cgggcccacg cacgcctgat ggccgggaaa ttgtcttcta caaagtgatc   1380
gactacatcc tccacggcaa ggaggagatc aaggtcattc ccacaccctc agccgatcac   1440
tgggccctgg ccagcggcct tccaagctac gtggcagaaa gcggctttat ttgtaacatc   1500
atgaatgctt ccgctgacga aatgttcaaa tttcaggaag gggccctgga cgactccggg   1560
tggctcatca agaatgtgct gtccatgccc atcgtcaaca agaaggagga gattgtggga   1620
gtcgccacat tttacaacag gaaagacggg aagccctttg acgaacagga cgaggttctc   1680
atggagtccc tgacacagtt cctgggctgg tcagtgatga acaccgacac ctacgacaag   1740
atgaacaagc tggagaaccg caaggacatc gcacaggaca tggtccttta ccacgtgaag   1800
tgcgacaggg acgagatcca gctcatcctg ccaaccagag cgcgcctggg aaggagcct   1860 gctgactgcg atgaggacga gctgggcgaa atcctgaagg aggagctgcc agggcccacc   1920
acatttgaca tctacgaatt ccacttctct gacctggagt gcaccgaact ggacctggtc   1980
aaatgtggca tccagatgta ctacgagctg ggcgtggtcc gaaagttcca gatcccccag   2040
gaggtcctgg tgcggttcct gttctccatc agcaaagggt accggagaat cacctaccac   2100
aactggcgcc acggcttcaa cgtggcccag acgatgttca cgctgctcat gaccggcaaa   2160
ctgaagagct actacacgga cctggaggcc ttcgccatgg tgacagccgg cctgtgccat   2220
gacatcgacc accgcggcac caacaacctg taccagatga agtcccagaa cccccttggct   2280 aagctccacg gctcctcgat tttgagcgg caccacctgg agtttgggaa gttcctgctc   2340
tcggaggaga ccctgaacat ctaccagaac ctgaaccggc ggcagcacga gcacgtgatc   2400
cacctgatgg acatcgccat catcgccacg gacctggccc tgtacttcaa gaagagagcg   2460
atgtttcaga agatcgtgga tgagtccaag aactaccagg acaagaagag ctgggtggag   2520
tacctgtccc tggagacgac ccggaaggag atcgtcatgg ccatgatgat gacagcctgc   2580
gacctgtctg ccatcaccaa gcccctgggaa gtccagagca aggtcgcact tctcgtggct   2640
gctgagttct gggagcaagg tgacttggaa aggacagtct tggatcagca gcccattcct   2700
atgatggacc ggaacaaggc ggccgagctc cccaagctgc aagtgggctt catcgacttc   2760
gtgtgcacat tcgtgtacaa ggagttctct cgtttccacg aagagatcct gcccatgttc   2820
gaccgactgc agaacaatag aaagagtgg aaggcgctgg ctgatgagta tgaggccaaa   2880
gtgaaggctc tggaggagaa ggaggaggag gagagggtgg cagccaagaa agtaggcaca   2940
gaaatttgca atggcggccc agcacccaag tcttcaacct gctgtatcct gtgagatatc   3000
agcgctttaa atttgcgcat gctagctata gttctagagg gcctattct atagtgtcac   3060 ctaaatgcta gagctcgctg atcagcctcg actgtgcctt ctagttgcca gccatctgtt   3120
gtttgcccct ccccgtgcc ttccttgacc ctggaaggtg ccactccac tgtcctttcc   3180 taataaaatg aggaaattgc atcgcattgt ctgagtaggt gtcattctat tctggggggt   3240
ggggtggggc aggacagcaa gggggaggat tgggaagaca atagcaggca tgctgggat   3300 gcggtgggct ctatggcttc tgaggcggaa agaaccaggt agataagtag catggcgggt   3360
```

| | | | | |
|---|---|---|---|---|
| taatcattaa | ctacaaggaa | cccctagtga | tggagttggc | cactccctct |
| ctgcgcgctc | | | | | 3420
| gctcgctcac | tgaggccggg | cgaccaaagg | tcgcccgacg | cccgggcttt |
| gcccgggcgg | | | | | 3480
| cctcagtgag | cgagcgagcg | cgcag | | | 3505

<210> SEQ ID NO 2
<211> LENGTH: 2565
<212> TYPE: DNA
<213> ORGANISM: Homo sapiens

<400> SEQUENCE: 2

| | | | | |
|---|---|---|---|---|
| atgagcctca | gtgaggagca | ggcccggagc | tttctggacc | agaaccccga | ttttgcccgc | 60
| cagtactttg | ggaagaaact | gagccctgag | aatgtggccg | cggcctgcga | ggacgggtgc | 120
| ccgccggact | gcgacagcct | ccgggacctc | tgccaggtgg | aggagagcac | ggcgctgctg | 180
| gagctggtgc | aggatatgca | ggagagcatc | aacatggagc | gcgtggtctt | caaggtcctg | 240
| cggcgcctct | gcaccctcct | gcaggccgac | cgctgcagcc | tcttcatgta | ccgccagcgc | 300
| aacggcgtgg | ccgagctggc | caccaggctt | ttcagcgtgc | agccggacag | cgtcctggag | 360
| gactgcctgg | tgcccccccga | ctccgagatc | gtcttcccac | tggacatcgg | ggtcgtgggc | 420
| cacgtggctc | agaccaaaaa | gatggtgaac | gtcgaggacg | tggccgagtg | ccctcacttc | 480
| agctcatttg | ctgacgagct | cactgactac | aagacaaaga | atatgctggc | cacacccatc | 540
| atgaatggca | agacgtcgt | ggcggtgatc | atggcagtga | caagctcaa | cggcccattc | 600
| ttcaccagcg | aagacgaaga | tgtgttcttg | aagtacctga | ttttgccac | gttgtacctg | 660
| aagatctatc | acctgagcta | cctccacaac | tgcgagacgc | gccgcggcca | ggtgctgctg | 720
| tggtcggcca | caaggtgtt | tgaggagctg | acggacatcg | agaggcagtt | ccacaaggcc | 780
| ttctacacgg | tgcgggccta | cctcaactgc | gagcggtact | ccgtgggcct | cctggacatg | 840
| accaaggaga | aggaattttt | tgacgtgtgg | tctgtgctga | tgggagagtc | ccagccgtac | 900
| tcgggcccac | gcacgcctga | tggccgggaa | attgtcttct | acaaagtgat | cgactacatc | 960
| ctccacggca | aggaggagat | caaggtcatt | cccacaccct | cagccgatca | ctgggccctg | 1020
| gccagcggcc | ttccaagcta | cgtggcagaa | agcggctttta | tttgtaacat | catgaatgct | 1080
| tccgctgacg | aaatgttcaa | atttcaggaa | ggggccctgg | acgactccgg | gtggctcatc | 1140
| aagaatgtgc | tgtccatgcc | catcgtcaac | aagaaggagg | agattgtggg | agtcgccaca | 1200
| ttttacaaca | ggaaagacgg | gaagcccttt | gacgaacagg | acgaggttct | catggagtcc | 1260
| ctgacacagt | tcctgggctg | gtcagtgatg | aacaccgaca | cctacgacaa | gatgaacaag | 1320
| ctggagaacc | gcaaggacat | cgcacaggac | atggtccttt | accacgtgaa | gtgcgacagg | 1380
| gacgagatcc | agctcatcct | gccaaccaga | gcgcgcctgg | ggaaggagcc | tgctgactgc | 1440
| gatgaggacg | agctgggcga | atcctgaag | gaggagctgc | agggcccac | cacatttgac | 1500
| atctacgaat | tccacttctc | tgacctggag | tgcaccgaac | tggacctggt | caaatgtggc | 1560
| atccagatgt | actacgagct | gggcgtggtc | cgaaagttcc | agatccccca | ggaggtcctg | 1620
| gtgcggttcc | tgttctccat | cagcaaaggg | taccggagaa | tcacctacca | caactggcgc | 1680
| cacggcttca | acgtggccca | gacgatgttc | acgctgctca | tgaccggcaa | actgaagagc | 1740
| tactacacgg | acctggaggc | cttcgccatg | gtgacagccg | gcctgtgcca | tgacatcgac | 1800
| caccgcggca | ccaacaacct | gtaccagatg | aagtcccaga | acccttggc | taagctccac | 1860
| ggctcctcga | ttttgagcg | gcaccacctg | gagtttggga | agttcctgct | ctcggaggag | 1920
| accctgaaca | tctaccagaa | cctgaaccgg | cggcagcacg | agcacgtgat | ccacctgatg | 1980

```
gacatcgcca tcatcgccac ggacctggcc ctgtacttca agaagagagc gatgtttcag    2040
aagatcgtgg atgagtccaa gaactaccag gacaagaaga gctgggtgga gtacctgtcc    2100
ctggagacga cccggaagga gatcgtcatg gccatgatga tgacagcctg cgacctgtct    2160
gccatcacca agccctggga agtccagagc aaggtcgcac ttctcgtggc tgctgagttc    2220
tgggagcaag gtgacttgga aaggacagtc ttggatcagc agcccattcc tatgatggac    2280
cggaacaagg cggccgagct ccccaagctg caagtgggct tcatcgactt cgtgtgcaca    2340
ttcgtgtaca aggagttctc tcgtttccac gaagagatcc tgcccatgtt cgaccgactg    2400
cagaacaata ggaaagagtg gaaggcgctg gctgatgagt atgaggccaa agtgaaggct    2460
ctggaggaga aggaggagga ggagagggtg gcagccaaga aagtaggcac agaaatttgc    2520
aatggcggcc cagcacccaa gtcttcaacc tgctgtatcc tgtga                   2565

<210> SEQ ID NO 3
<211> LENGTH: 130
<212> TYPE: DNA
<213> ORGANISM: Artificial Sequence
<220> FEATURE:
<223> OTHER INFORMATION: 5' ITR derived from AAV-2

<400> SEQUENCE: 3
ctgcgcgctc gctcgctcac tgaggccgcc cgggcaaagc ccgggcgtcg ggcgaccttt     60
ggccgggcgg cctcagtgag cgagcgagcg cgcagagagg gagtggccaa ctccatcact    120
aggggttcct                                                           130

<210> SEQ ID NO 4
<211> LENGTH: 130
<212> TYPE: DNA
<213> ORGANISM: Artificial Sequence
<220> FEATURE:
<223> OTHER INFORMATION: 3' ITR derived from AAV-2

<400> SEQUENCE: 4
aggaacccct agtgatggag ttggccactc cctctctgcg cgctcgctcg ctcactgagg     60
ccgggcgacc aaaggtcgcc cgacgcccgg gctttgcccg gcggcctcag tgagcgagc    120 gagcgcgcag                                                           130

<210> SEQ ID NO 5
<211> LENGTH: 242
<212> TYPE: DNA
<213> ORGANISM: Homo sapiens

<400> SEQUENCE: 5
actagtccgg atccaagctc agatctcgag ttgggcccca gaagcctggt ggttgtttgt     60
ccttctcagg ggaaaagtga ggcggcccct tggaggaagg ggccgggcag aatgatctaa    120
tcggattcca agcagctcag gggattgtct ttttctagca ccttcttgcc actcctaagc    180
gtcctccgtg accccggctg ggatttagcc tggtgctgtg tcagccccgg tcgacaagc    240 tt                                                                   242

<210> SEQ ID NO 6
<211> LENGTH: 225
<212> TYPE: DNA
<213> ORGANISM: Bos indicus

<400> SEQUENCE: 6
```

```
ctgtgccttc tagttgccag ccatctgttg tttgcccctc ccccgtgcct tccttgaccc      60
tggaaggtgc cactcccact gtcctttcct aataaaatga ggaaattgca tcgcattgtc     120
tgagtaggtg tcattctatt ctgggggtg gggtggggca ggacagcaag ggggaggatt     180
gggaagacaa tagcaggcat gctggggatg cggtgggctc tatgg                    225

<210> SEQ ID NO 7
<211> LENGTH: 3265
<212> TYPE: DNA
<213> ORGANISM: Artificial Sequence
<220> FEATURE:
<223> OTHER INFORMATION: Synthetic Expression cassette encoding human
      RPE65

<400> SEQUENCE: 7
ctctccaaga tccaacaaaa gtgattatac cccccaaaat atgatggtag tatcttatac      60
taccatcatt ttataggcat agggctctta gctgcaaata atggaactaa ctctaataaa     120
gcagaacgca aatattgtaa atattagaga gctaacaatc tctgggatgg ctaaaggatg     180
gagcttggag gctacccagc cagtaacaat attccgggct ccactgttga acggagacac     240
tacaactgcc ttggatgggc agagatatta tggatgctaa gccccaggtg ctaccattag     300
gacttctacc actgtcccta acgggtggag cccatcacat gcctatgccc tcactgtaag     360
gaaatgaagc tactgttgta tatcttggga agcacttgga ttaattgtta tacagttttg     420
ttgaagaaga ccccctaggggt aagtagccat aactgcacac taaatttaaa attgttaatg     480
agtttctcaa aaaaaatgtt aaggttgtta gctggtatag tatatatctt gcctgttttc     540
caaggacttc tttgggcagt accttgtctg tgctggcaag caactgagac ttaatgaaag     600
agtattggag atatgaatga attgatgctg tatactctca gagtgccaaa catataccaa     660
tggacaagaa ggtgaggcag agagcagaca ggcattagtg acaagcaaag atatgcagaa     720
tttcattctc agcaaatcaa aagtcctcaa cctggttgga agaatattgg cactgaatgg     780
tatcaataag gttgctagag agggttagag gtgcacaatg tgcttccata acattttata     840
cttctccaat cttagcacta atcaaacatg gttgaatagt ttgtttacta taactcttac     900
agagttataa gatctgtgaa gacagggaca gggacaatac ccatctctgt ctggttcata     960
ggtggtatgt aatagatatt tttaaaaata agtgagttaa tgaatgaggg tgagaatgaa    1020
ggcacagagg tattaggggg aggtgggccc cagagaatgg tgccaaggtc cagtgggtg    1080 actgggatca gctcaggcct gacgctggcc actcccacct agctcctttc tttctaatct    1140
gttctcattc tccttgggaa ggattgaggt ctctggaaaa cagccaaaca actgttatgg    1200
gaacagcaag cccaaataaa gccaagcatc aggggatct gagagctgaa agcaacttct    1260
gttccccctc cctcagctga aggggtgggg aagggctccc aaagccataa ctccttttaa    1320
gggatttaga aggcataaaa aggcccctgg ctgagaactt ccttcttcat tctgcagttg    1380
gtaatcacta gtaacggccg ccagcaagct tgaattcatg tctatccagg ttgagcatcc    1440
tgctggtggt tacaagaaac tgtttgaaac tgtggaggaa ctgtcctcgc cgctcacagc    1500
tcatgtaaca ggcaggatcc ccctctggct caccggcagt ctccttcgat gtgggccagg    1560
actctttgaa gttggatctg agccatttta ccacctgttt gatgggcaag ccctcctgca    1620
caagtttgac tttaagaag acatgtcac ataccacaga aggttcatcc gcactgatgc    1680
ttacgtacgg gcaatgactg agaaaaggat cgtcataaca gaatttggca cctgtgcttt    1740
cccagatccc tgcaagaata tattttccag gttttttttct tactttcgag gagtagaggt    1800
```

```
tactgacaat gcccttgtta atgtctaccc agtgggggaa gattactacg cttgcacaga    1860
gaccaacttt attacaaaga ttaatccaga gaccttggag acaattaagc aggttgatct    1920
ttgcaactat gtctctgtca atggggccac tgctcacccc acattgaaaa tgatggaac     1980 cgtttacaat attggtaatt gctttggaaa aaattttca attgcctaca acattgtaaa     2040
gatcccacca ctgcaagcag acaaggaaga tccaataagc aagtcagaga tcgttgtaca    2100
attcccctgc agtgaccgat tcaagccatc ttacgttcat agttttggtc tgactcccaa    2160
ctatatcgtt tttgtggaga caccagtcaa aattaacctg ttcaagttcc tttcttcatg    2220
gagtctttgg ggagccaact acatggattg ttttgagtcc aatgaaacca tgggggtttg    2280
gcttcatatt gctgacaaaa aaggaaaaa gtacctcaat aataaataca gaacttctcc     2340
tttcaacctc ttccatcaca tcaacaccta tgaagacaat gggtttctga ttgtggatct    2400
ctgctgctgg aaaggatttg agtttgttta taattactta tatttagcca atttacgtga    2460
gaactgggaa gaagtgaaaa aaaatgccag aaaggctccc caacctgaag ttaggagata    2520
tgtacttcct ttgaatattg acaaggctga cacaggcaag aatttagtca cgctccccaa    2580
tacaactgcc actgcaattc tgtgcagtga cgagactatc tggctggagc ctgaagttct    2640
cttttcaggg cctcgtcaag catttgagtt tcctcaaatc aattaccaga agtattgtgg    2700
gaaaccttac acatatgcgt atggacttgg cttgaatcac tttgttccag ataggctctg    2760
taagctgaat gtcaaaacta agaaaacttg ggtttggcaa gagcctgatt catacccatc    2820
agaacccatc tttgtttctc acccagatgc cttggaagaa gatgatggtg tagttctgag    2880
tgtggtggtg agcccaggag caggacaaaa gcctgcttat ctcctgattc tgaatgccaa    2940
ggacttaagt gaagttgccc gggctgaagt ggagattaac atccctgtca cctttcatgg    3000
actgttcaaa aaatcttgaa gcttggctga tcagcctcga ctgtgccttc tagttgccag    3060
ccatctgttg tttgcccctc ccccgtgcct tccttgaccc tggaaggtgc cactcccact    3120
gtccttccct aataaaatga ggaaattgca tcgcattgtc tgagtaggtg tcattctatt    3180 ctgggggtg gggtggggca ggacagcaag ggggaggatt gggaagacaa tagcaggcat    3240
gctggggatg cggtgggctc tatgg                                          3265
```

<210> SEQ ID NO 8
<211> LENGTH: 1382
<212> TYPE: DNA
<213> ORGANISM: Homo sapiens

<400> SEQUENCE: 8

```
ctctccaaga tccaacaaaa gtgattatac ccccccaaaat atgatggtag tatcttatac     60
taccatcatt ttataggcat agggctctta gctgcaaata atggaactaa ctctaataaa    120
gcagaacgca atattgtaa atattagaga gctaacaatc tctgggatgg ctaaaggatg     180
gagcttggag gctacccagc cagtaacaat attccgggct ccactgttga acggagacac    240
tacaactgcc ttggatgggc agagatatta tggatgctaa gccccaggtg ctaccattag    300
gacttctacc actgtcccta acgggtggag cccatcacat gcctatgccc tcactgtaag    360
gaaatgaagc tactgttgta tatcttggga agcacttgga ttaattgtta tacagttttg    420
ttgaagaaga ccccctaggggt aagtagccat aactgcacac taaatttaaa attgttaatg    480
agtttctcaa aaaaaatgtt aaggttgtta gctggtatag tatatatctt gcctgttttc    540
caaggacttc tttgggcagt accttgtctg tgctggcaag caactgagac ttaatgaaag    600
agtattggag atatgaatga attgatgctg tatactctca gagtgccaaa catataccaa    660
```

```
tggacaagaa ggtgaggcag agagcagaca ggcattagtg acaagcaaag atatgcagaa      720
tttcattctc agcaaatcaa aagtcctcaa cctggttgga agaatattgg cactgaatgg      780
tatcaataag gttgctagag agggttagag gtgcacaatg tgcttccata acattttata      840
cttctccaat cttagcacta atcaaacatg gttgaatagt ttgtttacta taactcttac      900
agagttataa gatctgtgaa gacagggaca gggacaatac ccatctctgt ctggttcata      960
ggtggtatgt aatagatatt tttaaaaata agtgagttaa tgaatgaggg tgagaatgaa     1020
ggcacagagg tattagggggg aggtgggccc cagagaatgg tgccaaggtc cagtggggtg     1080
actgggatca gctcaggcct gacgctggcc actcccacct agctcctttc tttctaatct     1140
gttctcattc tccttgggaa ggattgaggt ctctggaaaa cagccaaaca actgttatgg     1200
gaacagcaag cccaaataaa gccaagcatc agggggatct gagagctgaa agcaacttct     1260
gttccccctc cctcagctga aggggtgggg aagggctccc aaagccataa ctccttttaa     1320
gggatttaga aggcataaaa aggcccctgg ctgagaactt ccttcttcat tctgcagttg     1380
gt                                                                     1382

<210> SEQ ID NO 9
<211> LENGTH: 1602
<212> TYPE: DNA
<213> ORGANISM: Homo sapiens

<400> SEQUENCE: 9
atgtctatcc aggttgagca tcctgctggt ggttacaaga aactgtttga aactgtggag       60
gaactgtcct cgccgctcac agctcatgta acaggcagga tccccctctg gctcaccggc      120
agtctccttc gatgtgggcc aggactcttt gaagttggat ctgagccatt ttaccacctg      180
tttgatgggc aagccctcct gcacaagttt gactttaaag aaggacatgt cacataccac      240
agaaggttca tccgcactga tgcttacgta cgggcaatga ctgagaaaag gatcgtcata      300
acagaatttg gcacctgtgc tttcccagat ccctgcaaga atatattttc caggtttttt      360
tcttactttc gaggagtaga ggttactgac aatgcccttg ttaatgtcta cccagtgggg      420
gaagattact acgcttgcac agagaccaac tttattacaa agattaatcc agagaccttg      480
gagacaatta gcaggttgaa tctttgcaac tatgtctctg tcaatggggc cactgctcac      540
ccccacattg aaaatgatgg aaccgtttac aatattggta attgctttgg aaaaaatttt      600
tcaattgcct acaacattgt aaagatccca ccactgcaag cagacaagga agatccaata      660
agcaagtcag agatcgttgt acaattcccc tgcagtgacc gattcaagcc atcttacgtt      720
catagttttg gtctgactcc caactatatc gttttttgtgg agacaccagt caaaattaac      780
ctgttcaagt tcctttcttc atggagtctt tggggagcca actacatgga ttgttttgag      840
tccaatgaaa ccatgggggt ttggcttcat attgctgaca aaaaaggaa aaagtacctc      900 aataataaat acagaacttc tccttttcaac ctcttccatc acatcaacac ctatgaagac      960
aatgggtttc tgattgtgga tctctgctgc tggaaaggat ttgagtttgt ttataattac     1020
ttatatttag ccaatttacg tgagaactgg gaagaagtga aaaaaatgc cagaaaggct     1080 ccccaacctg aagttaggag atatgtactt cctttgaata ttgacaaggc tgacacaggc     1140
aagaatttag tcacgctccc caatacaact gccactgcaa ttctgtgcag tgacgagact     1200
atctggctgg agcctgaagt tctcttttca gggcctcgtc aagcatttga gtttcctcaa     1260
atcaattacc agaagtattg tgggaaacct tacacatatg cgtatggact tggcttgaat     1320
```

| | |
|---|---|
| cactttgttc cagataggct ctgtaagctg aatgtcaaaa ctaaagaaac ttgggtttgg | 1380 |
| caagagcctg attcataccc atcagaaccc atctttgttt ctcacccaga tgccttggaa | 1440 |
| gaagatgatg gtgtagttct gagtgtggtg gtgagcccag gagcaggaca aaagcctgct | 1500 |
| tatctcctga ttctgaatgc caaggactta agtgaagttg cccgggctga agtggagatt | 1560 |
| aacatccctg tcacctttca tggactgttc aaaaaatctt ga | 1602 |

<210> SEQ ID NO 10
<211> LENGTH: 2205
<212> TYPE: DNA
<213> ORGANISM: Artificial Sequence
<220> FEATURE:
<223> OTHER INFORMATION: VP1 coding sequence derived from AAV4

<400> SEQUENCE: 10

| | |
|---|---|
| atgactgacg gttaccttcc agattggcta gaggacaacc tctctgaagg cgttcgagag | 60 |
| tggtgggcgc tgcaacctgg agcccctaaa cccaaggcaa atcaacaaca tcaggacaac | 120 |
| gctcggggtc ttgtgcttcc gggttacaaa tacctcggac ccggcaacgg actcgacaag | 180 |
| ggggaacccg tcaacgcagc ggacgcggca gccctcgagc acgacaaggc ctacgaccag | 240 |
| cagctcaagg ccggtgacaa cccctacctc aagtacaacc acgccgacgc ggagttccag | 300 |
| cagcggcttc agggcgacac atcgtttggg ggcaacctcg gcagagcagt cttccaggcc | 360 |
| aaaaagaggg ttcttgaacc tcttggtctg gttgagcaag cgggtgagac ggctcctgga | 420 |
| aagaagagac cgttgattga atcccccag cagcccgact cctccacggg tatcggcaaa | 480 |
| aaaggcaagc agccggctaa aaagaagctc gtttttcgaag acgaaactgg agcaggcgac | 540 |
| ggaccccctg agggatcaac ttccggagcc atgtctgatg acagtgagat gcgtgcagca | 600 |
| gctggcggag ctgcagtcga gggcggacaa ggtgccgatg gagtgggtaa tgcctcgggt | 660 |
| gattggcatt gcgattccac ctggtctgag gccacgtca cgaccaccag caccagaacc | 720 |
| tgggtcttgc ccacctacaa caaccacctc tacaagcgac tcggagagag cctgcagtcc | 780 |
| aacacctaca acggattctc cacccctgg ggatactttg acttcaaccg cttccactgc | 840 |
| cacttctcac acgtgactg gcagcgactc atcaacaaca ctggggcat gcgacccaaa | 900 |
| gccatgcggg tcaaaatctt caacatccag gtcaaggagg tcacgacgtc gaacggcgag | 960 |
| acaacggtgg ctaataacct taccagcacg gttcagatct ttgcggactc gtcgtacgaa | 1020 |
| ctgccgtacg tgatggatgc gggtcaagag gcagcctgc ctccttttcc caacgacgtc | 1080 |
| tttatggtgc cccagtacgg ctactgtgga ctggtgaccg caacacttc gcagcaacag | 1140 |
| actgacagaa atgccttcta ctgcctggag tactttccttt cgcagatgct gcggactggc | 1200 |
| aacaactttg aaattacgta cagtttttgag aaggtgcctt tccactcgat gtacgcgcac | 1260 |
| agccagagcc tggaccggct gatgaaccct ctcatcgacc agtacctgtg gggactgcaa | 1320 |
| tcgaccacca ccggaaccac cctgaatgcc gggactgcca ccaccaactt taccaagctg | 1380 |
| cggcctacca actttccaa ctttaaaag aactggctgc ccgggccttc aatcaagcag | 1440 |
| cagggcttct caaagactgc caatcaaaac tacaagatcc ctgccaccgg gtcagacagt | 1500 |
| ctcatcaaat acgagacgca cagcactctg acggaagat ggagtgccct gacccccgga | 1560 |
| cctccaatgg ccacggctgg acctgcggac agcaagttca gcaacagcca gctcatcttt | 1620 |
| gcggggcctg aacagaacgg caacgcggcc accgtacccg ggactctgat cttcacctct | 1680 |
| gaggaggagc tggcagccac caacgccacc gatacggaca tgtggggcaa cctacctggc | 1740 |
| ggtgaccaga gcaacagcaa cctgccgacc gtggacagac tgacagccct gggagccgtg | 1800 |

```
cctggaatgg tctggcaaaa cagagacatt tactaccagg gtcccatttg ggccaagatt    1860
cctcataccg atggacactt tcacccctca ccgctgattg gtgggtttgg gctgaaacac    1920
ccgcctcctc aaattttat caagaacacc ccggtacctg cgaatcctgc aacgaccttc     1980
agctctactc cggtaaactc cttcattact cagtacagca ctggccaggt gtcggtgcag    2040
attgactggg agatccagaa ggagcggtcc aaacgctgga accccgaggt ccagtttacc    2100
tccaactacg acagcaaaaa ctctctgttg tgggctcccg atgcggctgg gaaatacact    2160
gagcctaggg ctatcggtac ccgctacctc acccaccacc tgtaa                   2205

<210> SEQ ID NO 11
<211> LENGTH: 1797
<212> TYPE: DNA
<213> ORGANISM: Artificial Sequence
<220> FEATURE:
<223> OTHER INFORMATION: VP2 coding sequence derived from AAV4

<400> SEQUENCE: 11
acggctcctg gaaagaagag accgttgatt gaatcccccc agcagcccga ctcctccacg    60
ggtatcggca aaaaggcaa gcagccggct aaaaagaagc tcgttttcga agacgaaact     120
ggagcaggcg acggaccccc tgagggatca acttccggag ccatgtctga tgacagtgag    180
atgcgtgcag cagctggcgg agctgcagtc gagggcggac aaggtgccga tggagtgggt    240
aatgcctcgg gtgattggca ttgcgattcc acctggtctg agggccacgt cacgaccacc    300
agcaccagaa cctgggtctt gcccacctac aacaaccacc tctacaagcg actcggagag    360
agcctgcagt ccaacaccta caacggattc tccacccccct ggggatactt tgacttcaac    420
cgcttccact gccacttctc accacgtgac tggcagcgac tcatcaacaa caactggggc    480
atgcgaccca agccatgcg ggtcaaaatc ttcaacatcc aggtcaagga ggtcacgacg    540
tcgaacggcg agacaacggt ggctaataac cttaccagca cggttcagat ctttgcggac    600
tcgtcgtacg aactgccgta cgtgatggat gcgggtcaag agggcagcct gcctcctttt    660
cccaacgacg tctttatggt gccccagtac ggctactgtg gactggtgac cggcaacact    720
tcgcagcaac agactgacag aaatgccttc tactgcctgg agtactttcc ttcgcagatg    780
ctgcggactg gcaacaactt tgaaattacg tacagttttg agaaggtgcc tttccactcg    840
atgtacgcgc acagccagag cctggaccgg ctgatgaacc ctctcatcga ccagtacctg    900
tggggactgc aatcgaccac caccggaacc accctgaatg ccgggactgc caccaccaac    960
tttaccaagc tgcggcctac caactttttcc aactttaaaa agaactgggct gcccgggcct    1020 tcaatcaagc agcagggctt ctcaaagact gccaatcaaa actacaagat ccctgccacc    1080
gggtcagaca gtctcatcaa atacgagacg cacagcactc tggacggaag atggagtgcc    1140
ctgacccccg gacctccaat ggccacggct ggacctgcgg acagcaagtt cagcaacagc    1200
cagctcatct tgcggggcc tgaacagaac ggcaacacgg ccaccgtacc cgggactctg    1260
atcttcacct ctgaggagga gctggcagcc accaacgcca ccgatacgga catgtggggc    1320
aacctacctg gcggtgacca gagcaacagc aacctgccga ccgtggacag actgacagcc    1380
ttgggagccg tgcctggaat ggtctggcaa aacagagaca tttactacca gggtcccatt    1440
tgggccaaga ttcctcatac cgatggacac tttcacccct caccgctgat tgtgggtttt    1500
gggctgaaac accgcctcc tcaaattttt atcaagaaca cccggtacc tgcgaatcct    1560 gcaacgacct tcagctctac tccggtaaac tccttcatta ctcagtacag cactggccag    1620
```

```
gtgtcggtgc agattgactg ggagatccag aaggagcggt ccaaacgctg gaaccccgag    1680
gtccagttta cctccaacta cggacagcaa aactctctgt tgtgggctcc cgatgcggct    1740
gggaaataca ctgagcctag ggctatcggt acccgctacc tcacccacca cctgtaa      1797

<210> SEQ ID NO 12
<211> LENGTH: 1617
<212> TYPE: DNA
<213> ORGANISM: Artificial Sequence
<220> FEATURE:
<223> OTHER INFORMATION: VP3 coding sequence derived from AAV4

<400> SEQUENCE: 12
atgcgtgcag cagctggcgg agctgcagtc gagggcggac aaggtgccga tggagtgggt      60
aatgcctcgg gtgattggca ttgcgattcc acctggtctg agggccacgt cacgaccacc     120
agcaccagaa cctgggtctt gcccacctac aacaaccacc tctacaagcg actcggagag     180
agcctgcagt ccaacaccta caacggattc tccaccccct ggggatactt tgacttcaac     240
cgcttccact gccacttctc accacgtgac tggcagcgac tcatcaacaa caactgggga     300
atgcgaccca agccatgcg gtcaaaatc ttcaacatcc aggtcaagga ggtcacgacg     360
tcgaacggcg agacaacggt ggctaataac cttaccagca cggttcagat ctttgcggac     420
tcgtcgtacg aactgccgta cgtgatggat gcgggtcaag agggcagcct gcctcctttt     480
cccaacgacg tctttatggt gcccagtac ggctactgtg actggtgac cggcaacact     540 tcgcagcaac agactgacag aaatgccttc tactgcctgg agtactttcc ttcgcagatg     600
ctgcggactg gcaacaactt tgaaattacg tacagttttg agaaggtgcc ttttcactcg     660
atgtacgcgc acagccagag cctggaccgg ctgatgaacc ctctcatcga ccagtacctg     720
tggggactgc aatcgaccac caccggaacc accctgaatg ccgggactgc caccaccaac     780
tttaccaagc tgcggcctac caacttttcc aactttaaaa agaactggct gcccgggcct     840
tcaatcaagc agcagggctt ctcaaagact gccaatcaaa actacaagat ccctgccacc     900
gggtcagaca gtctcatcaa atacgagacg cacagcactc tggacggaag atggagtgcc     960 ctgaccccg acctccaat ggccacggct ggacctgcgg acagcaagtt cagcaacagc    1020
cagctcatct ttgcggggcc tgaacagaac ggcaacacgg ccaccgtacc cgggactctg    1080
atcttcacct ctgaggagga gctggcagcc accaacgcca ccgatacgga catgtgggc    1140 aacctacctg gcggtgacca gagcaacagc aacctgccga ccgtggacag actgacagcc    1200
ttgggagccg tgcctggaat ggtctggcaa aacagagaca tttactacca gggtcccatt    1260
tgggccaaga ttcctcatac cgatggacac tttcacccct caccgctgat tggtgggttt    1320
gggctgaaac accgcctcc tcaaattttt atcaagaaca cccgggtacc tgcgaatcct    1380
gcaacgacct tcagctctac tccggtaaac tccttcatta ctcagtacag cactggccag    1440
gtgtcggtgc agattgactg ggagatccag aaggagcggt ccaaacgctg gaaccccgag    1500
gtccagttta cctccaacta cggacagcaa aactctctgt tgtgggctcc cgatgcggct    1560
gggaaataca ctgagcctag ggctatcggt acccgctacc tcacccacca cctgtaa      1617

<210> SEQ ID NO 13
<211> LENGTH: 2175
<212> TYPE: DNA
<213> ORGANISM: Artificial Sequence
<220> FEATURE:
<223> OTHER INFORMATION: VP1 coding sequence derived from AAV5

<400> SEQUENCE: 13
```

```
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc ttttggcctg gttgaagagg gtgctaagac ggcccctacc     420
ggaaagcgga tagacgacca cttttccaaaa agaaagaagg ctcggaccga agaggactcc    480
aagccttcca cctcgtcaga cgccgaagct ggacccagcg atcccagca gctgcaaatc      540
ccagcccaac cagcctcaag tttgggagct gatacaatgt ctgcgggagg tggcggccca     600
tgggcgaca ataaccaagg tgccgatgga gtgggcaatg cctcgggaga ttggcattgc      660
gattccacgt ggatggggga cagagtcgtc accaagtcca cccgaacctg ggtgctgccc     720
agctacaaca accaccagta ccgagagatc aaaagcggct ccgtcgacgg aagcaacgcc     780
aacgcctact ttggatacag cacccccctgg gggtactttg actttaaccg cttccacagc   840
cactggagcc cccgagactg gcaaagactc atcaacaact actggggctt cagacccccgg   900
tccctcagag tcaaaatctt caacattcaa gtcaaagagg tcacggtgca ggactccacc     960
accaccatcg ccaacaacct cacctccacc gtccaagtgt ttacggacga cgactaccag    1020
ctgccctacg tcgtcggcaa cgggaccgag ggatgcctgc cggccttccc tccgcaggtc    1080
tttacgctgc cgcagtacgg ttacgcgacg ctgaaccgcg acaacacaga aaatcccacc    1140
gagaggagca gcttcttctg cctagagtac tttcccagca agatgctgag aacgggcaac    1200
aactttgagt ttacctacaa ctttgaggag gtgcccttcc actccagctt cgctcccagt    1260
cagaacctgt tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttcccggg gcccatgggc cgaacccagg gctggaacct gggctccggg    1440
gtcaaccgcg ccagtgtcag cgccttcgcc acgaccaata ggatggagct cgagggcgcg    1500
agttaccagg tgcccccgca gccgaacggc atgaccaaca acctccaggg cagcaacacc    1560
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca cgtgtggat ggagagggac     1800
gtgtacctcc aaggacccat ctgggccaag atcccagaga cggggcgca ctttcacccc    1860
tctccggcca tgggcggatt cggactcaaa cacccaccgc ccatgatgct catcaagaac    1920
acgcctgtgc ccggaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca acgacccca gtttgtggac     2100
tttgccccgg acagcaccgg ggaatacaga accaccagac ctatcggaac ccgatacctt    2160
acccgacccc tttaa                                                     2175
```

<210> SEQ ID NO 14
<211> LENGTH: 1767
<212> TYPE: DNA

<213> ORGANISM: Artificial Sequence
<220> FEATURE:
<223> OTHER INFORMATION: VP2 coding sequence derived from AAV5

<400> SEQUENCE: 14

```
acggcccta ccggaaagcg gatagacgac cactttccaa aaagaaagaa ggctcggacc      60
gaagaggact ccaagccttc cacctcgtca gacgccgaag ctggaccag cggatcccag     120
cagctgcaaa tcccagccca accagcctca agtttgggag ctgatacaat gtctgcggga    180
ggtggcggcc cattgggcga caataaccaa ggtgccgatg gagtgggcaa tgcctcggga    240
gattggcatt gcgattccac gtggatgggg gacagagtcg tcaccaagtc cacccgaacc    300
tgggtgctgc ccagctacaa caaccaccag taccgagaga tcaaaagcgg ctccgtcgac    360
ggaagcaacg ccaacgccta ctttggatac agcaccccct gggggtactt tgactttaac    420
cgcttccaca gccactggag cccccgagac tggcaaagac tcatcaacaa ctactgggc    480
ttcagacccc ggtccctcag agtcaaaatc ttcaacattc aagtcaaaga ggtcacggtg    540
caggactcca ccaccaccat cgccaacaac ctcacctcca ccgtccaagt gtttacggac    600
gacgactacc agctgcccta cgtcgtcggc aacgggaccg agggatgcct gccggccttc    660
cctccgcagg tctttacgct gccgcagtac ggttacgcga cgctgaaccg cgacaacaca    720
gaaaatccca ccgagaggag cagcttcttc tgcctagagt actttcccag caagatgctg    780
agaacgggca caactttga gtttacctac aactttgagg aggtgccctt ccactccagc    840
ttcgctccca gtcagaacct gttcaagctg gccaacccgc tggtggacca gtacttgtac    900
cgcttcgtga gcacaaataa cactggcgga gtccagttca caagaacct ggccgggaga    960
tacgccaaca cctacaaaaa ctggttcccg ggcccatgg ccgaaccca gggctggaac    1020
ctgggctccg gggtcaaccg cgccagtgtc agcgccttcg ccacgaccaa taggatggag   1080
ctcgagggcg cgagttacca ggtgcccccg cagccgaacg gcatgaccaa caacctccag   1140
ggcagcaaca cctatgccct ggagaacact atgatcttca acagccagcc ggcgaacccg   1200
ggcaccaccg ccacgtacct cgagggcaac atgctcatca ccagcgagag cgagacgcag   1260
ccggtgaacc gcgtggcgta caacgtcggc gggcagatgg ccaccaacaa ccagagctcc   1320
accactgccc ccgcgaccgg cacgtacaac ctccaggaaa tcgtgccgg cagcgtgtgg   1380
atggagaggg acgtgtacct ccaaggaccc atctgggcca agatcccaga cgggggcg    1440
cactttcacc cctctccggc catgggcgga ttcggactca acacccacc gcccatgatg   1500
ctcatcaaga acacgcctgt gcccggaaat atcaccagct ctcggacgt gcccgtcagc   1560
agcttcatca cccagtacag caccgggcag gtcaccgtgg agatggagtg ggagctcaag   1620
aaggaaaact ccaagaggtg gaacccgag atccagtaca caaacaacta caacgacccc   1680
cagtttgtgg actttgcccc ggacagcacc ggggaataca gaaccaccag acctatcgga   1740
acccgatacc ttacccgacc cctttaa                                       1767
```

<210> SEQ ID NO 15
<211> LENGTH: 1599
<212> TYPE: DNA
<213> ORGANISM: Artificial Sequence
<220> FEATURE:
<223> OTHER INFORMATION: VP3 coding sequence derived from AAV5

<400> SEQUENCE: 15

```
atgtctgcgg gaggtggcgg cccattgggc gacaataacc aaggtgccga tggagtgggc      60
aatgcctcgg gagattggca ttgcgattcc acgtggatgg gggacagagt cgtcaccaag    120
```

-continued

```
tccacccgaa cctgggtgct gcccagctac aacaaccacc agtaccgaga gatcaaaagc    180
ggctccgtcg acggaagcaa cgccaacgcc tactttggat acagcacccc ctggggggtac   240 tttgacttta accgcttcca cagccactgg agccccgag actggcaaag actcatcaac    300
aactactggg gcttcagacc ccggtccctc agagtcaaaa tcttcaacat tcaagtcaaa    360
gaggtcacgg tgcaggactc caccaccacc atcgccaaca acctcacctc caccgtccaa    420
gtgtttacgg acgacgacta ccagctgccc tacgtcgtcg gcaacgggac cgagggatgc    480
ctgccggcct tccctccgca ggtctttacg ctgccgcagt acggttacgc gacgctgaac    540
cgcgacaaca cagaaaatcc caccgagagg agcagcttct tctgcctaga gtactttccc    600
agcaagatgc tgagaacggg caacaacttt gagtttacct acaactttga ggaggtgccc    660
ttccactcca gcttcgctcc cagtcagaac ctgttcaagc tggccaaccc gctggtggac    720
cagtacttgt accgcttcgt gagcacaaat aacactggcg gagtccagtt caacaagaac    780
ctggccggga gatacgccaa cacctacaaa aactggttcc cggggcccat gggccgaacc    840
cagggctgga acctgggctc cggggtcaac cgcgccagtg tcagcgcctt cgccacgacc    900
aataggatgg agctcgaggg cgcgagttac caggtgcccc cgcagccgaa cggcatgacc    960
aacaacctcc agggcagcaa cacctatgcc ctggagaaca ctatgatctt caacagccag   1020
ccggcgaacc cgggcaccac cgccacgtac ctcgagggca acatgctcat caccagcgag   1080
agcgagacgc agccggtgaa ccgcgtggcg tacaacgtcg gcgggcagat ggccaccaac    1140
aaccagagct ccaccactgc ccccgcgacc ggcacgtaca acctccagga aatcgtgccc    1200
ggcagcgtgt ggatggagag ggacgtgtac ctccaaggac ccatctgggc caagatccca    1260
gagacggggg cgcactttca cccctctccg gccatgggcg gattcggact caaacaccca    1320
ccgcccatga tgctcatcaa gaacacgcct gtgcccggaa atatcaccag cttctcggac    1380
gtgcccgtca gcagcttcat cacccagtac agcaccgggc aggtcaccgt ggagatggag    1440
tgggagctca agaaggaaaa ctccaagagg tggaacccag agatccagta cacaaacaac    1500
tacaacgacc cccagtttgt ggactttgcc ccggacagca cggggaata cagaaccacc    1560 agacctatcg gaacccgata ccttacccga cccctttaa                           1599
```